US005525258A

United States Patent [19]

Wingen et al.

[11] Patent Number: 5,525,258
[45] Date of Patent: Jun. 11, 1996

[54] TRIFLUOROPHENYLENE COMPOUNDS, PROCESS FOR THEIR PREPARATION, AND THEIR USE IN LIQUID-CRYSTALLINE MIXTURES

[75] Inventors: Rainer Wingen, Hattersheim/Main; Ralf Pfirmann, Griesheim, both of Germany

[73] Assignee: Hoechst Aktiengesellschaft, Germany

[21] Appl. No.: 425,260

[22] Filed: Apr. 18, 1995

Related U.S. Application Data

[62] Division of Ser. No. 168,053, Dec. 15, 1993, abandoned.

[30] Foreign Application Priority Data

Dec. 17, 1992 [DE] Germany .................. 42 42 695.2
Jun. 23, 1993 [DE] Germany .................. 43 20 755.3

[51] Int. Cl.[6] .......... C09K 19/52; C09K 19/12; C07C 19/08; G02F 1/13
[52] U.S. Cl. .................. 252/299.01; 252/299.61; 252/299.63; 252/299.66; 252/299.67; 359/103; 570/128; 570/144
[58] Field of Search .................. 252/299.01, 299.61, 252/299.63, 299.64, 299.65, 299.66; 570/128, 144; 359/103

[56] References Cited

U.S. PATENT DOCUMENTS 4,551,264  11/1985  Eidenschink et al. ............. 252/299.62
5,213,710  5/1993  Reiffenrath et al. ............. 212/299.63

FOREIGN PATENT DOCUMENTS 0090183   10/1983  European Pat. Off.
0500210A2  8/1992  European Pat. Off.
4111765A1  4/1992  Germany.
4037519A1  5/1992  Germany.
4127450A1  10/1992  Germany.
WO-A-8902425  3/1989  WIPO.
WO-A-8906678  7/1989  WIPO.
WO-A-8909203  10/1989  WIPO.

OTHER PUBLICATIONS

FE 68 "Some New Chiral Dopants Useful to Obtain Broad Range Sc* Mixtures", 12 Int. LCC, Freiburg 1988.
*Liquid Crystals, Applications and Uses.* vol. 1, B. Bahadur (ed.), p. 307, World Scientific, Singapore 1990. (Cited in Amendment filed May 16, 1994).

*Primary Examiner*—Shean C. Wu
*Attorney, Agent, or Firm*—Curtis, Morris & Safford

[57] ABSTRACT

Trifluorophenylene compounds of the formula (I)

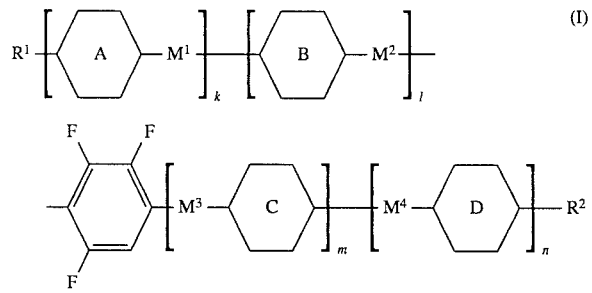

in which

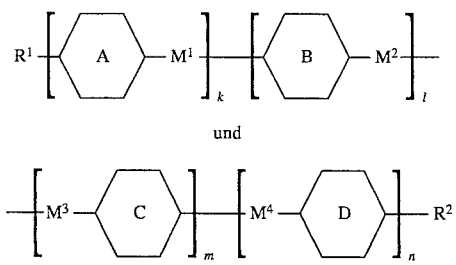

are mesogenic radicals, are useful components for liquid-crystal mixtures.

8 Claims, No Drawings

TRIFLUOROPHENYLENE COMPOUNDS, PROCESS FOR THEIR PREPARATION, AND THEIR USE IN LIQUID-CRYSTALLINE MIXTURES

This application is a division of application Ser. No. 08/168,053, filed Dec. 15, 1993 now abandoned.

BACKGROUND OF THE INVENTION

Particularly in the last decade, liquid crystals have been introduced into various industrial areas in which electro-optical and display-device properties are required (for example in watch, calculator and typewriter displays). These display devices are based on dielectric alignment effects in the nematic, cholesteric and/or smectic phases of the liquid-crystalline compounds, where—caused by the dielectric anisotropy—the molecular long axis of the compounds adopts a preferential alignment in an applied electric field. The usual response times in these display devices are too long for many other potential areas of application of liquid crystals. This disadvantage is particularly noticeable if a large number of pixels must be addressed. Production costs of equipment containing relatively large screen areas, for example of video equipment, are then generally too high.

In addition to nematic and cholesteric liquid crystals, optically active smectic liquid crystal phases have also been increasing in importance over the last few years.

Clark and Lagerwall were able to show that the use of ferroelectric liquid-crystal systems in very thin cells results in electro-optical switching or display elements which have response times faster by a factor of 1000 compared with conventional TN ("twisted nematic") cells (cf., for example, Lagerwall et al., "Ferroelectric Liquid Crystals for Displays", SID Symposium, October Meeting 1985, San Diego, Calif., USA). On the basis of this and other favorable properties, for example the possibility of bistable switching and the virtually viewing angle-independent contrast, FLCs are in principle highly suitable for the abovementioned areas of application, for example via matrix addressing.

For electro-optical or fully optical components, either compounds are required which form tilted or orthogonal smectic phases and are themselves optically active, or ferroelectric smectic phases can be induced by doping compounds which, although forming such smectic phases, are not themselves optically active, with optically active compounds. The desired phase should be stable over the broadest possible temperature range.

In order to achieve good contrast in electro-optical components, a uniform planar alignment of the liquid crystals is necessary. Good alignment in the $S_A$ and $S^*_c$ phase can be achieved if the phase sequence of the liquid-crystal mixture is, with decreasing temperature:

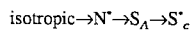

isotropic→N*→$S_A$→$S^*_c$

The prerequisite is that the pitch of the helix in the N* phase is very large (greater than 10 µm) or even better is fully compensated (see, for example, T. Matsumoto et al., pp. 468–470, Proc. of the 6th Int. Display Research Conf., Japan Display, Sep. 30–Oct. 2, 1986, Tokyo, Japan; M. Murakami et al., ibid. pp. 344–347). This is achieved by adding a further optically active dope which induces a right-hand helix to the chiral liquid-crystal mixture which has, for example, a left-hand helix in the N* phase, in such amounts that the helix is just compensated.

A further prerequisite for the use of the SSFLCD effect (surface-stabilized ferroelectric liquid-crystal display) of Clark and Lagerwall for uniform planar alignment is that the pitch in the smectic C* phase is significantly greater than the thickness of the display element (Mol. Cryst. Liq. Cryst. 94 (1983), 213–233 and 114 (1984), 151–187). As in the case of the cholesteric pitch, this is achieved by using dopes having the opposite rotation of the helix.

Ferroelectric liquid-crystal displays can also be operated by utilizing the DHF (distorted helix formation) effect or the PSFLCD effect (pitch-stabilized ferroelectric liquid-crystal display, also known as SBF=short pitch bistable ferroelectric effect). The DHF effect has been described by B. I. Ostrovski in Advances in Liquid Crystal Research and Applications, Oxford/Budapest, 1980, 469 ff.; the PSFLCD effect is described in DE-A 3 920 625 and EP 0 405 346 A2. In contrast to the SSFLCD effect, utilization of these effects requires a liquid-crystalline material having a short $S_c$ pitch.

The optical response time τ[µs] of ferroelectric liquid-crystal systems, which should be as short as possible, depends on the rotational viscosity of the system γ[mPas], the spontaneous polarization $P_s$[nC/cm$^2$] and the electric field strength E[V/m], in accordance with the equation $$\tau \sim \frac{\gamma}{P_s \cdot E}$$

Since the field strength E is determined by the electrode separation in the electro-optical component and by the applied voltage, the ferroelectric display medium must have low viscosity and a high spontaneous polarization to achieve a short response time.

Finally, in addition to thermal, chemical and photochemical stability, a small optical anisotropy Δn, preferably ≈0.13, and a low positive or preferably negative dielectric anisotropy Δε are required (see S. T. Lagerwall et al., "Ferroelectric Liquid Crystals for Displays", SID Symposium, Oct. Meeting 1985, San Diego, Calif., USA).

The totality of these requirements can only be achieved by means of mixtures comprising a plurality of components. The base (or matrix) used preferably comprises compounds which if possible themselves already have the desired phase sequence I→N→$S_A$→$S_c$. Further components of the mixtures are frequently added in order to reduce the melting point and to broaden the $S_c$ and usually also the N phase, to induce spontaneous polarization, for pitch compensation and to match the optical and dielectric anisotropy; however, the rotational viscosity, for example, should if possible not be increased.

Polyfluorinated phenyl derivatives have already been described a number of times as components of liquid-crystal mixtures, for example derivatives of 1,2-difluorophenylene in EP-B 357 702 and EP-A 500 210, derivatives of 1,3-difluorophenylene in DE-A 4 127 450, derivatives of 1,2,3,4-tetrafluorophenylene in DE-A 4 037 519, derivatives of 1,2,4,5-tetrafluoro-phenylene (presented at the 12th International Liquid Crystal Conference, 1988, Freiburg, Abstract FE 68, and WO 89/09203), and specific dopes containing a 1,2,4-trifluorophenylene or 1,2,4,5-tetrafluorophenylene unit in JP-A 5-17406.

Since, however, the development of ferroelectric liquid-crystal mixtures in particular can in no way be regarded as complete, the manufacturers of displays are interested in a very wide variety of components for mixtures. Another reason for this is that only the interaction of the liquid-crystalline mixtures with the individual components of the display device or of the cells (for example the alignment layer) allows conclusions to be drawn on the quality of the liquid-crystalline mixtures too.

SUMMARY OF THE INVENTION

The object of the present invention was therefore to provide novel compounds which are suitable in liquid-crystalline mixtures for improving the property profile of these mixtures.

This object is achieved according to the invention by means of trifluorophenylene compounds of the formula I

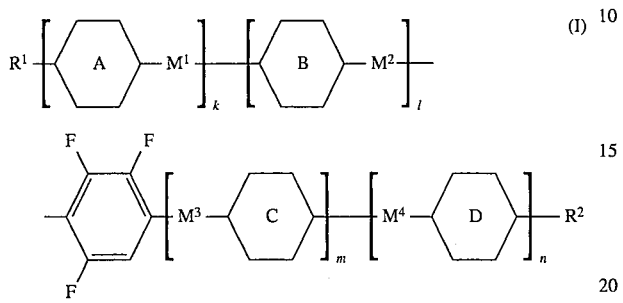

in which the symbols and indices have the following meanings:

$R^1$ and $R^2$ are, independently of one another, hydrogen, —CN, —$CF_3$, —$OCF_3$, —$OCF_2H$, —F, —Cl or a straight-chain or branched alkyl radical having 1 to 20 carbon atoms (with or without asymmetrical carbon atoms), where one or more $CH_2$ groups may also be replaced by —O—, —S—, —CO—, —CH=CH—, —C≡C—, Δ, —$Si(CH_3)_2$—, 1,4-phenylene, trans-1,4-cyclohexylene or trans-1,3-cyclopentylene, with the proviso that oxygen atoms and sulfur atoms (referred to as chalcogens below) must not be bonded directly to one another, and/or where one or more H atoms of the alkyl radical may be substituted by —F, —Cl, —Br or —$OR^3$; or are one of the radicals listed below:

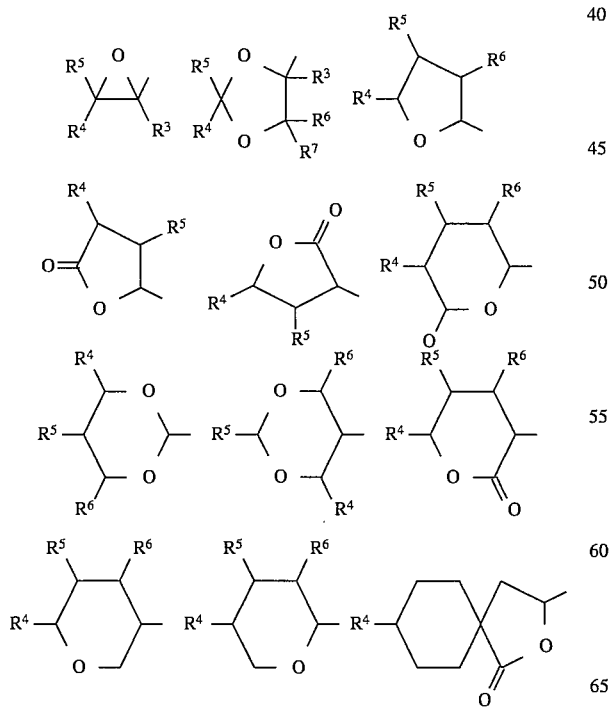

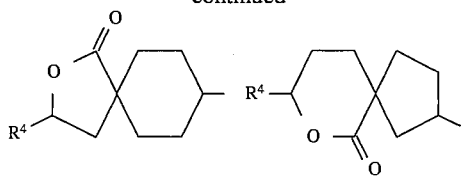

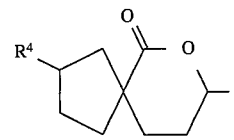

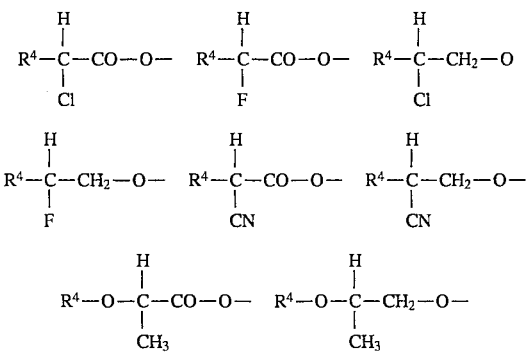

$R^3$, $R^4$, $R^5$, $R^6$ and $R^7$ are, independently of one another, hydrogen or a straight-chain or branched alkyl radical having 1–16 carbon atoms (with or without asymmetrical carbon atoms), where one or more $CH_2$ groups may also be replaced by —O— or —CH=CH— (with the proviso that oxygen atoms must not be bonded directly to one another) and/or one or more H atoms of the alkyl radical may be substituted by —F or —Cl; $R^4$ and $R^5$ together may also be —$(CH_2)_4$— or —$(CH_2)_5$— if they are bonded to an oxirane, dioxolane, tetrahydrofuran, tetrahydropyran, butyrolactone or valerolactone system;

$M^1$, $M^2$, $M^3$ and $M^4$ are identical or different and are —CO—O—, —O—, —O—CO—, —OOC—$CH_2$—$CH_2$—, —$CH_2$—$CH_2$—COO—, —$(CH_2)_4$—, —$O(CH_2)_3$—, —$(CH_2)_3O$—, —$CH_2$—O—, —O—$CH_2$—, —CH=CH—, —C≡C— or a single bond;

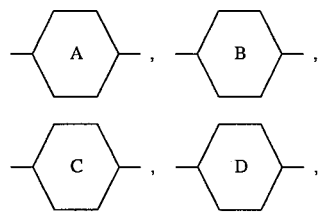

are identical or different and are 1,4-phenylene, in which one, two, three or four H atoms may be replaced by F, Cl and/or CN, pyrazine-2,5-diyl, pyridazine-3,6-diyl, pyridine-2,5-diyl, in which one H atom may also be replaced by F, pyrimidine-2,5-diyl, in which one H atom may also be replaced by F, trans-1,4-cyclohexylene, in which one or two H atoms may be replaced by CN and/or $CH_3$, 1,3,4-thiadiazole-2,5-diyl, 1,3-dioxane-2,5-diyl, 1,3-thiazole-2,4-diyl, 1,3-thiazole-2,5-diyl, thiophene-2,4-diyl, -thiophene-2,5-diyl, piperazine-1,4-diyl, piperazine-2,5-diyl, naphthalene-2,6- diyl, bicyclo[2.2.2]octane-1,4-diyl or 1,3-dioxaborinane-2,5-diyl;

k, l, m and n are zero or one, with the proviso that the sum k+l+m+n is 1, 2 or 3.

DESCRIPTION OF THE PREFERRED EMBODIMENTS

Preference is given to the compounds of the sub-structure (Ia)

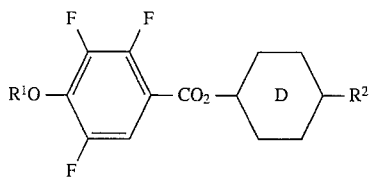

and of these particularly preferably to the compounds

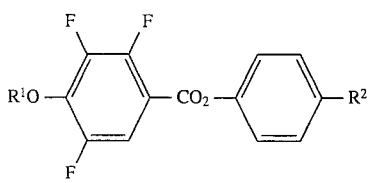

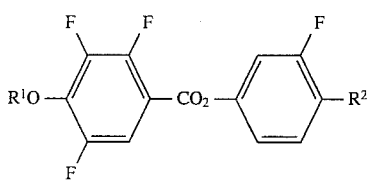

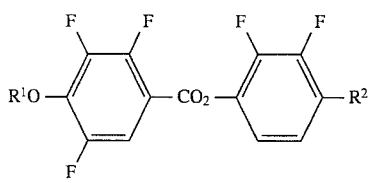

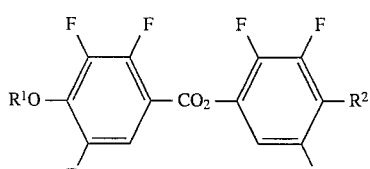

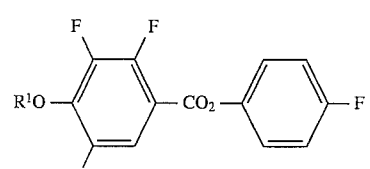

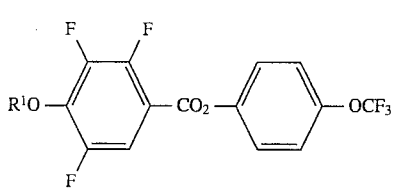

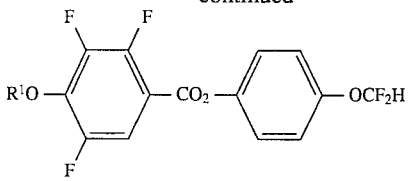

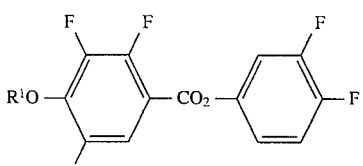

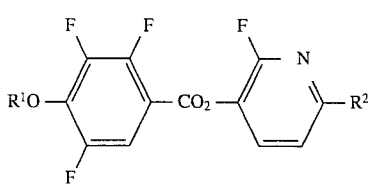

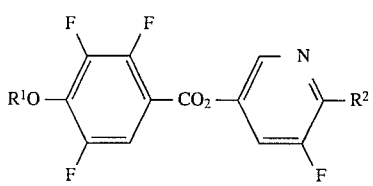

Preference is furthermore given to the compounds of the sub-structure

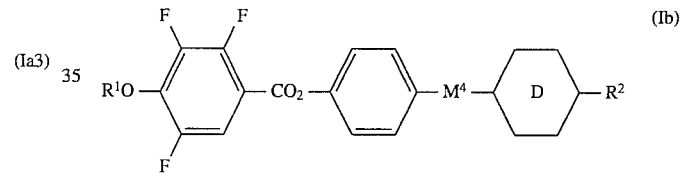

and of these particular preference is given to the compounds

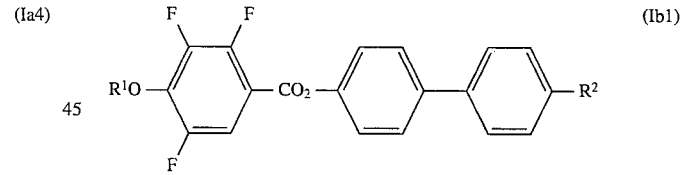

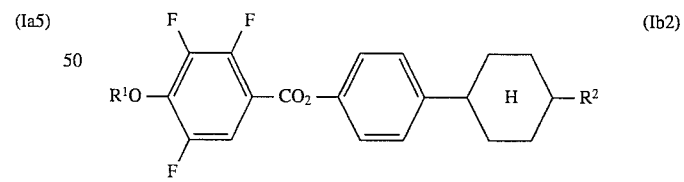

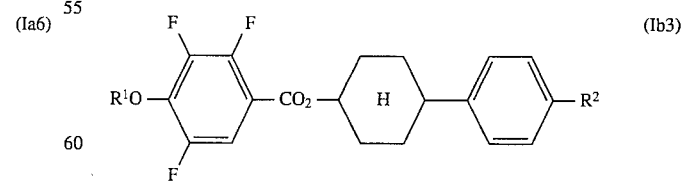

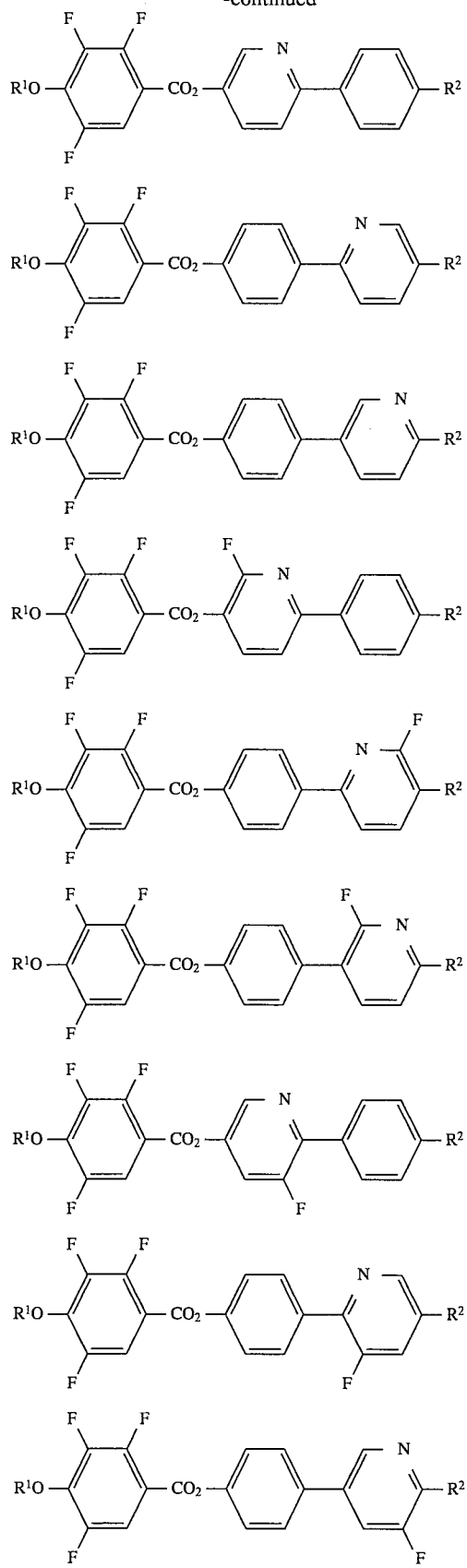
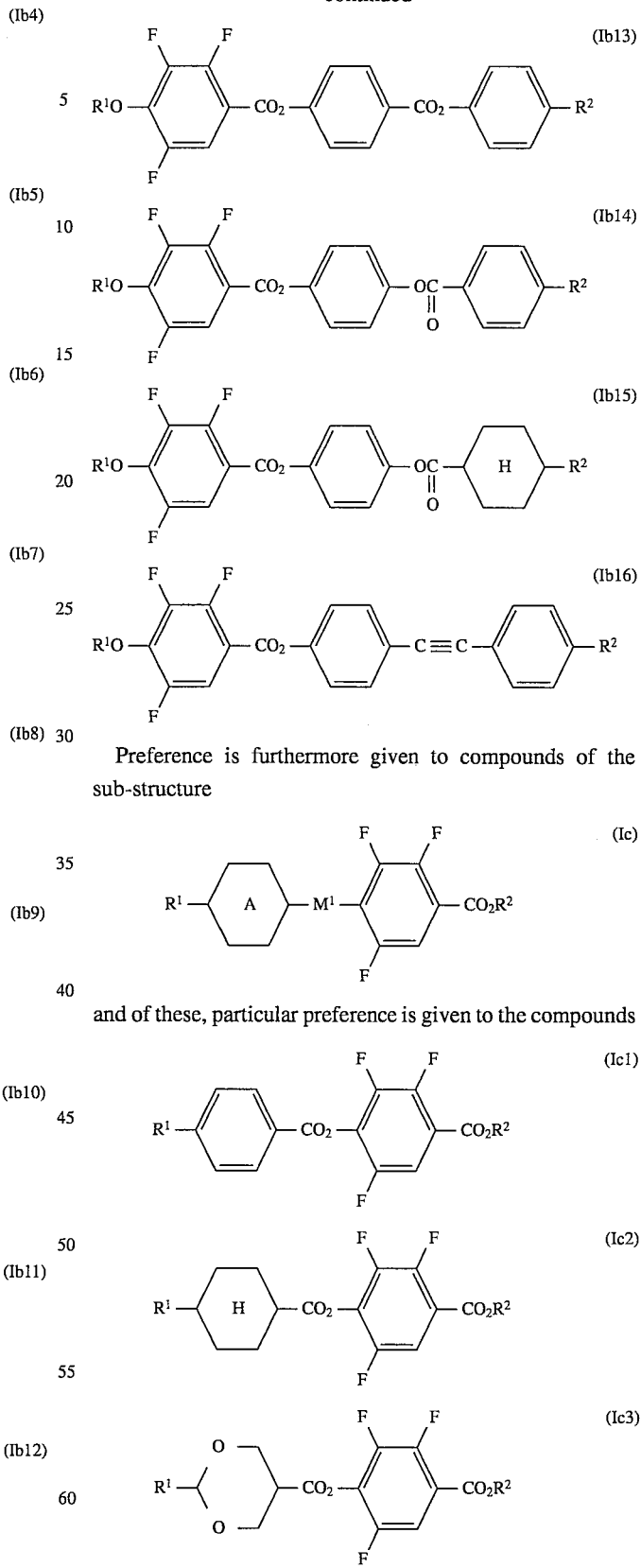
Preference is furthermore given to compounds of the sub-structure
and of these, particular preference is given to the compounds

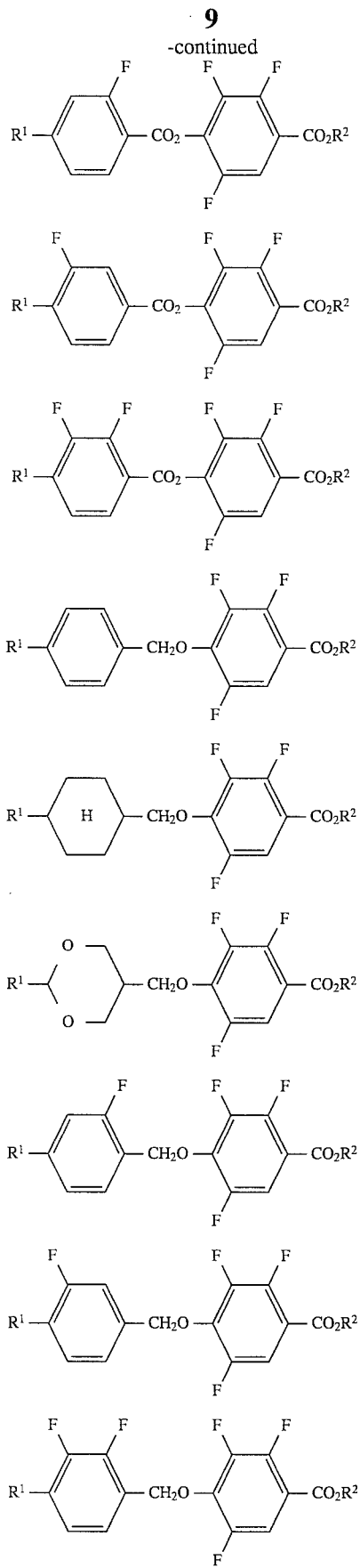
Preference is furthermore given to compounds of the formula (Id)
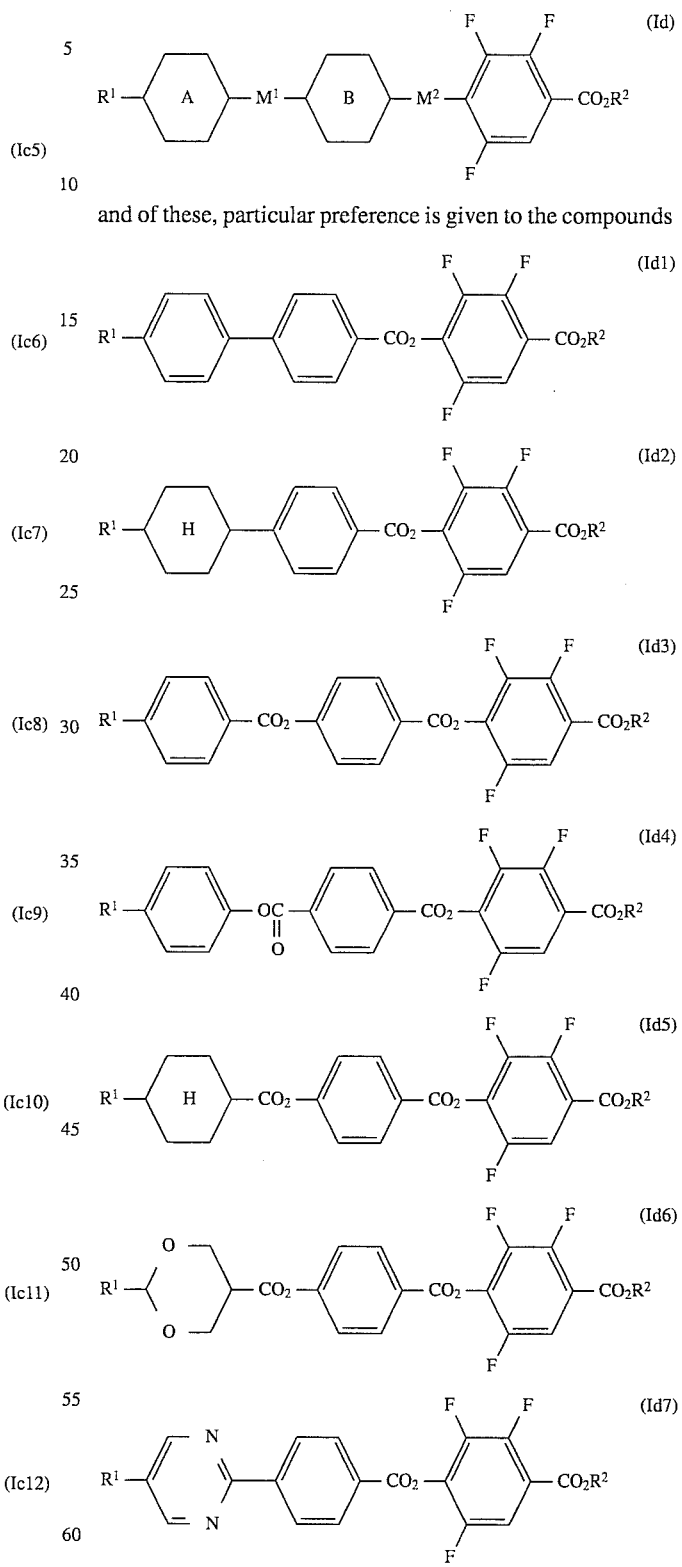
and of these, particular preference is given to the compounds

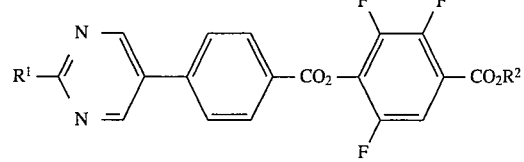 (Id8)
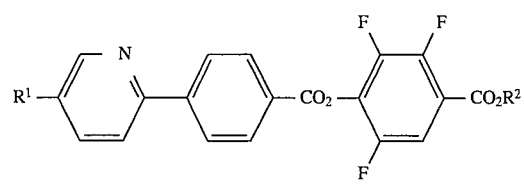 (Id9)
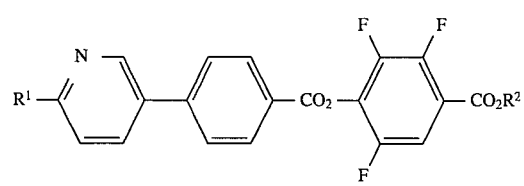 (Id10)
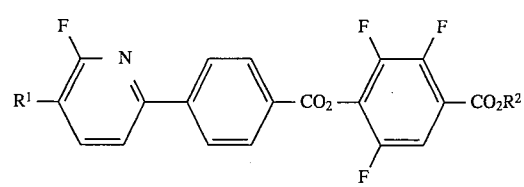 (Id11)
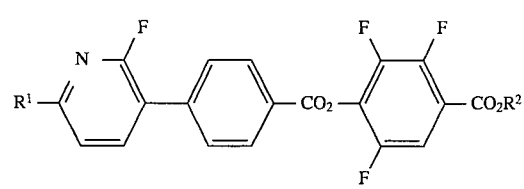 (Id12)
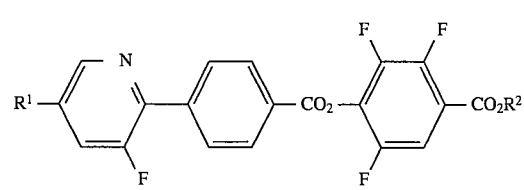 (Id13)
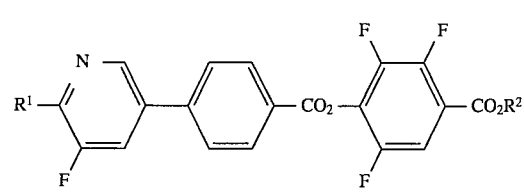 (Id14)
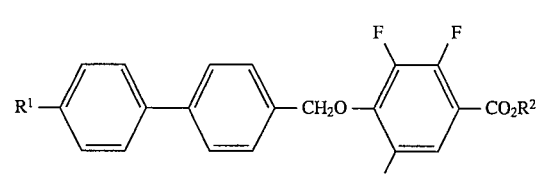 (Id15)
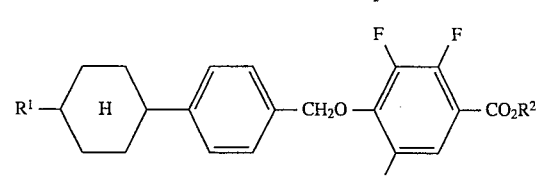 (Id16)
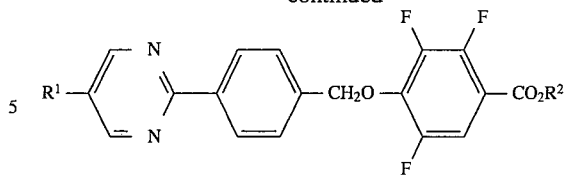 (Id17)
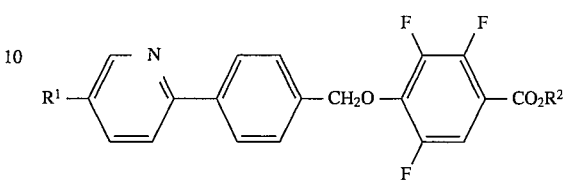 (Id18)
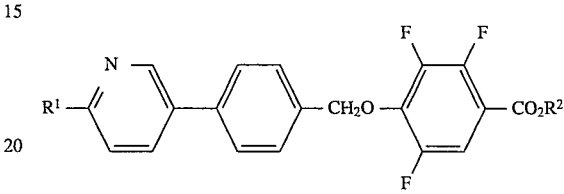 (Id19)
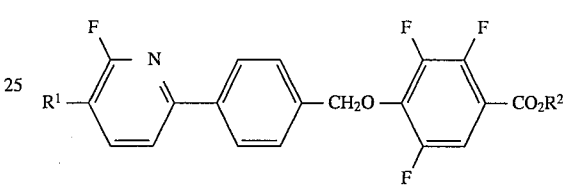 (Id20)
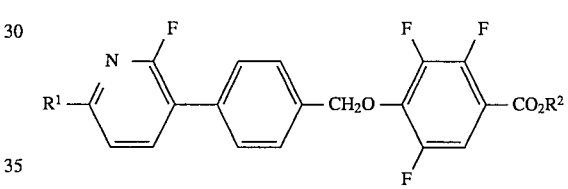 (Id21)
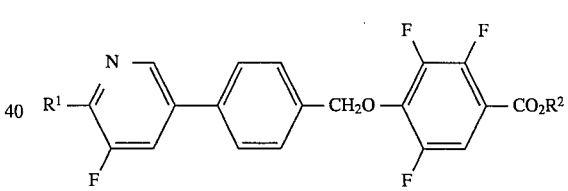 (Id22)
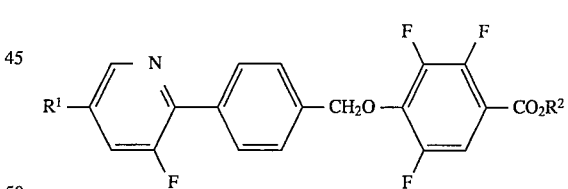 (Id23)
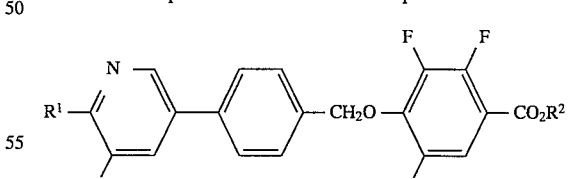 (Id24)
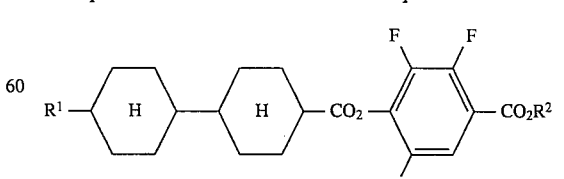 (Id25)

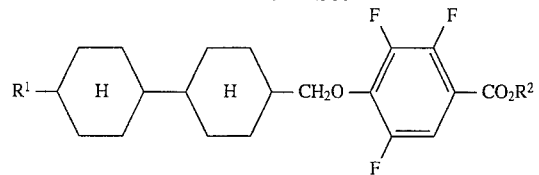
(Id26)
Preference is furthermore given to the compounds of the formula
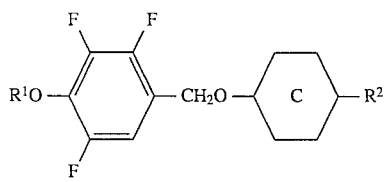
(Ie)
and of these, particular preference is given to the compounds
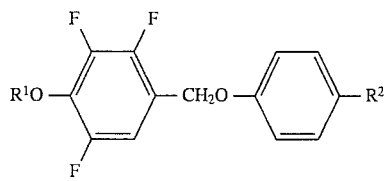
(Ie1)
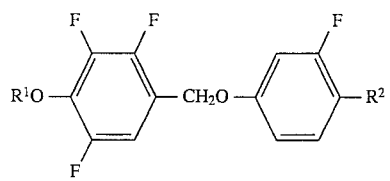
(Ie2)
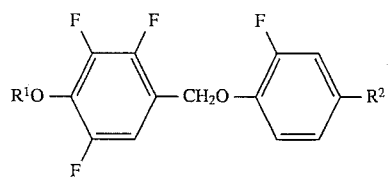
(Ie3)
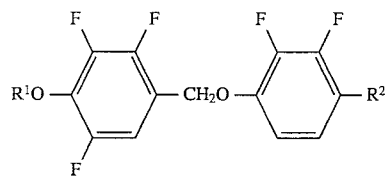
(Ie4)
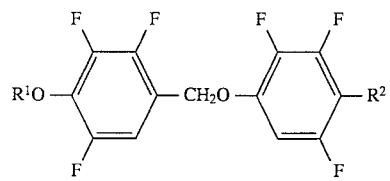
(Ie5)
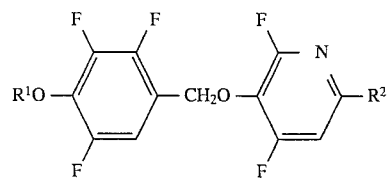
(Ie6)
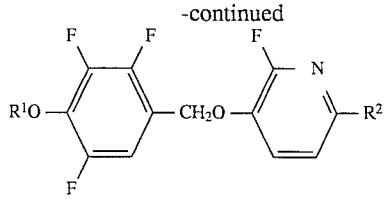
(Ie7)
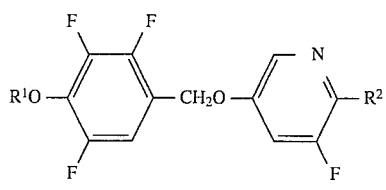
(Ie8)
Preference is furthermore given to the compounds of the formula
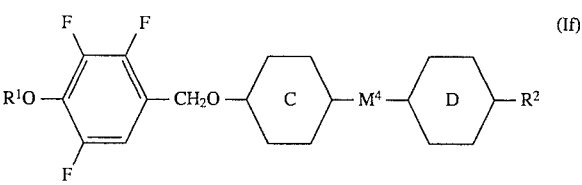
(If)
and of these, particular preference is given to the compounds
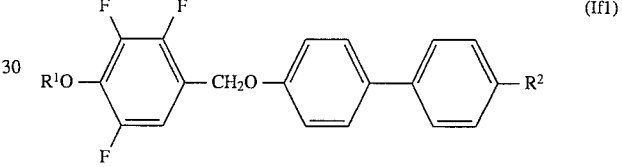
(If1)
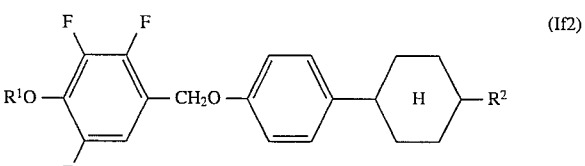
(If2)
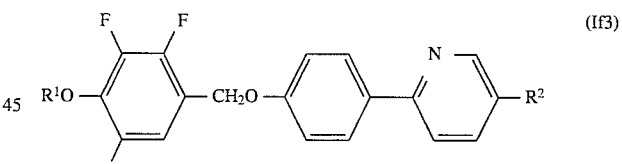
(If3)
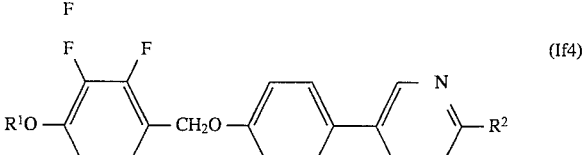
(If4)
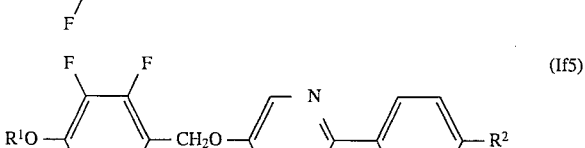
(If5)

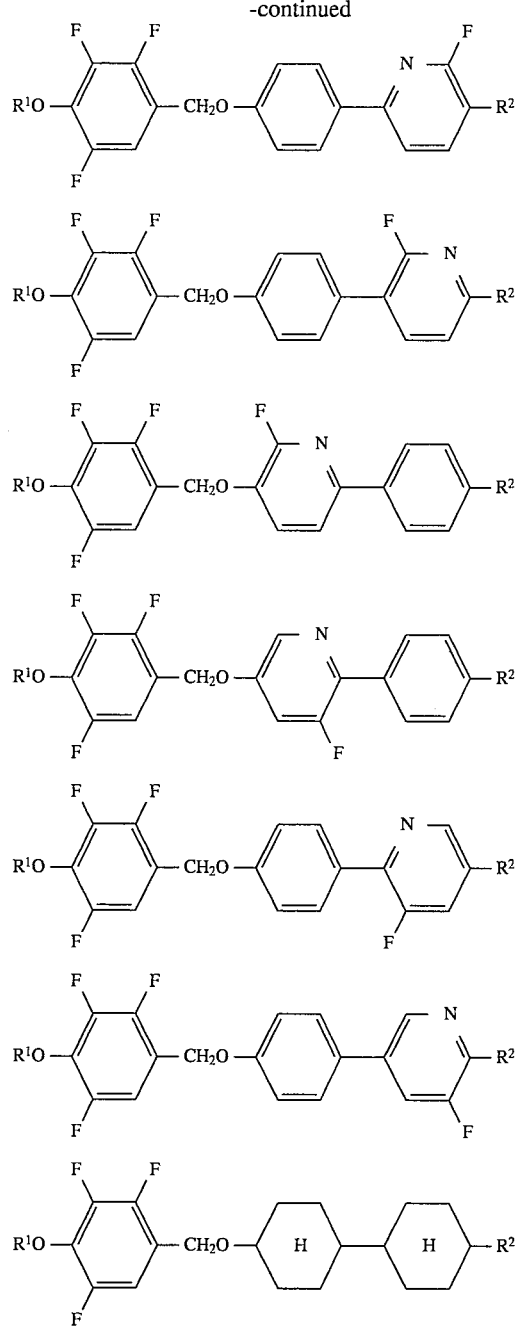
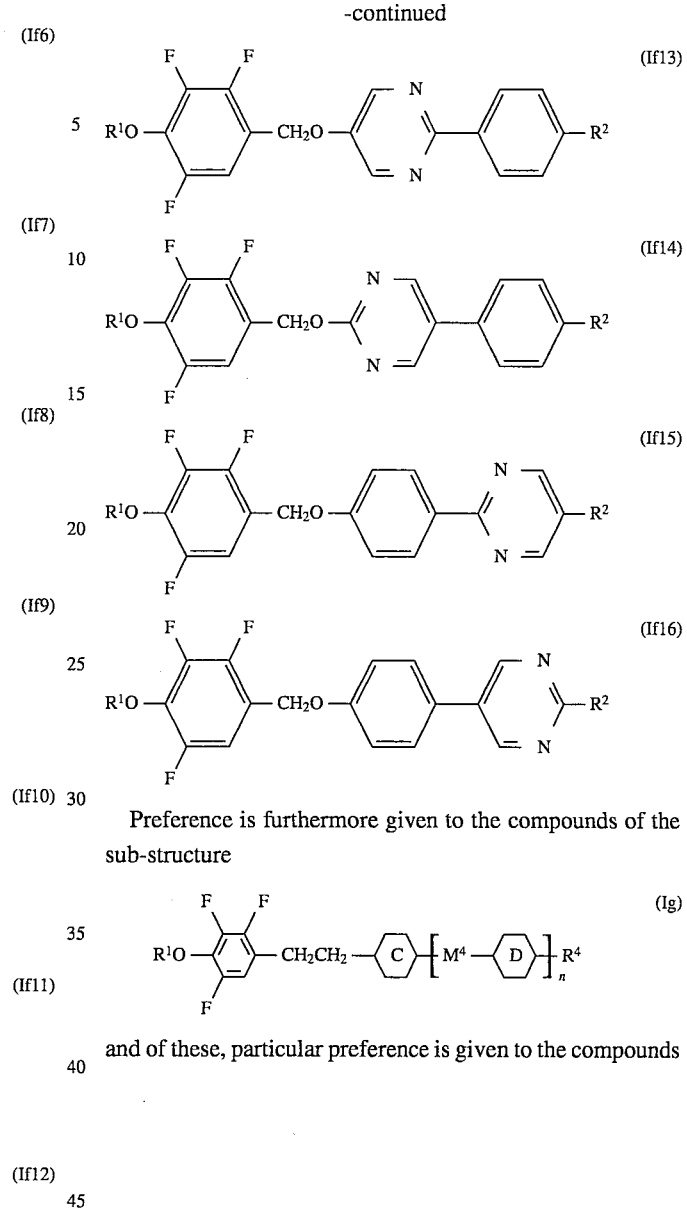
Preference is furthermore given to the compounds of the sub-structure
and of these, particular preference is given to the compounds
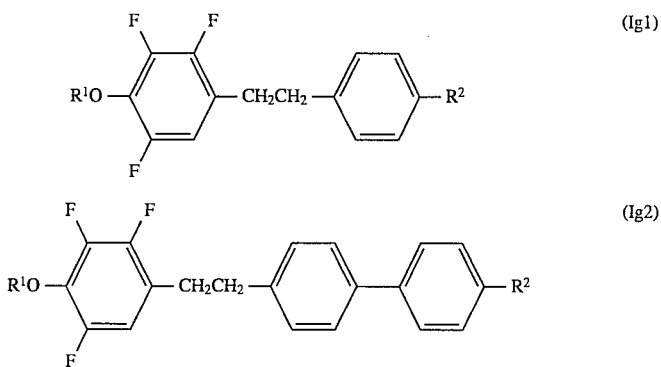

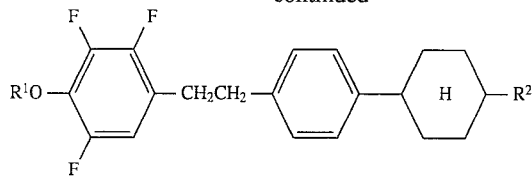
(Ig3)
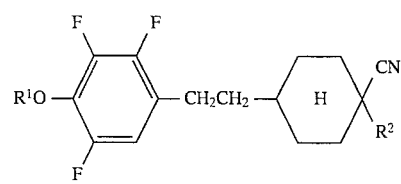
(Ig4)
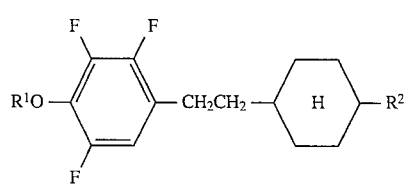
(Ig5)
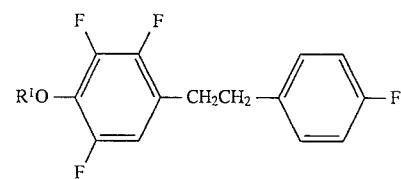
(Ig6)
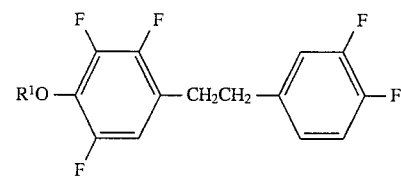
(Ig7)
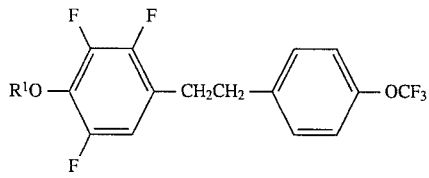
(Ig8)
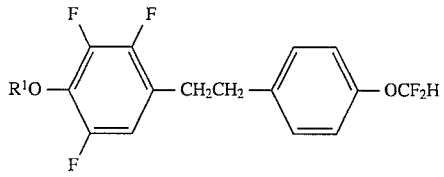
(Ig9)
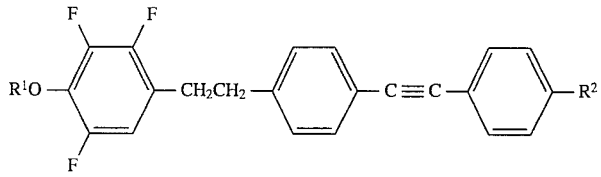
(Ig10)
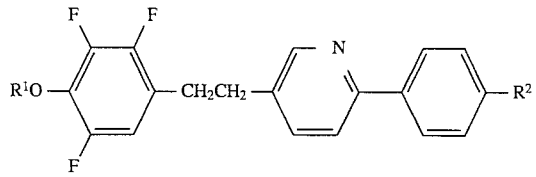
(Ig11)

-continued
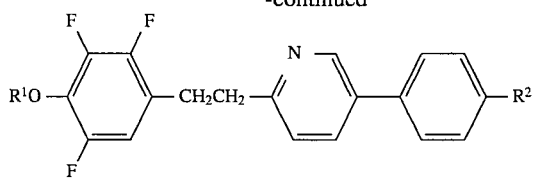
(Ig12)
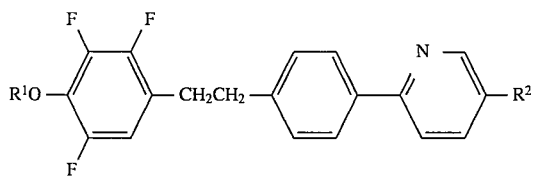
(Ig13)
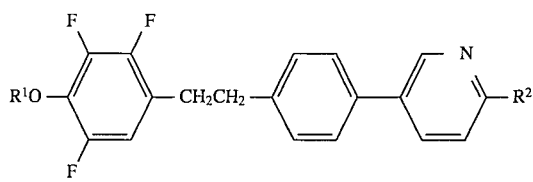
(Ig14)
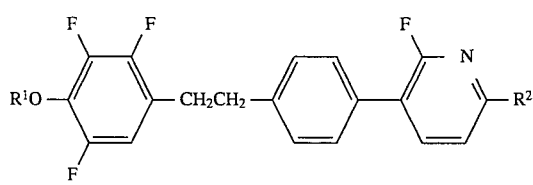
(Ig15)
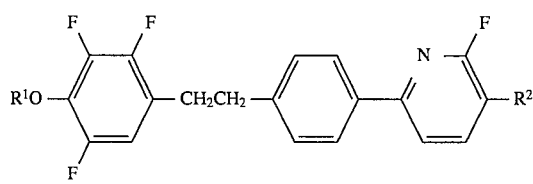
(Ig16)
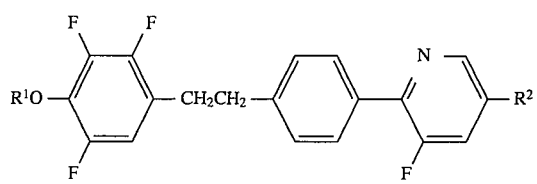
(Ig17)
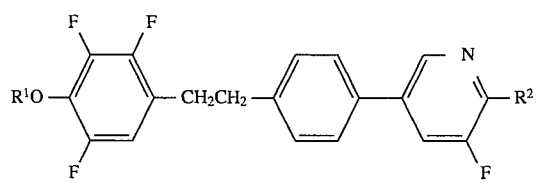
(Ig18)
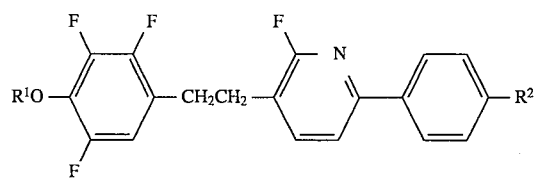
(Ig19)
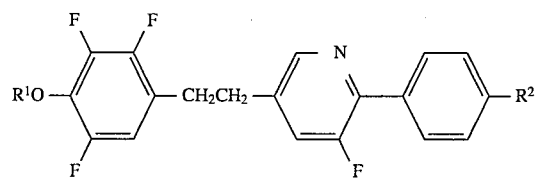
(Ig20)

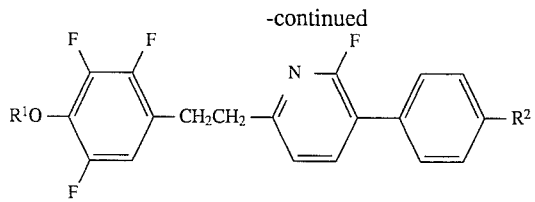
(Ig21)
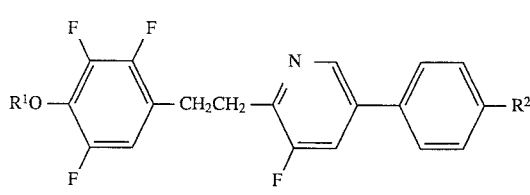
(Ig22)
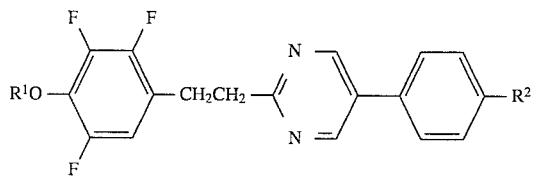
(Ig23)
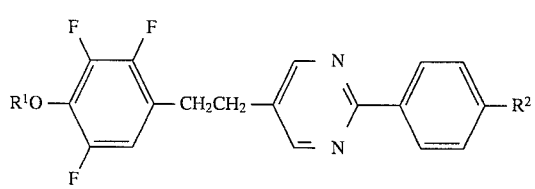
(Ig24)
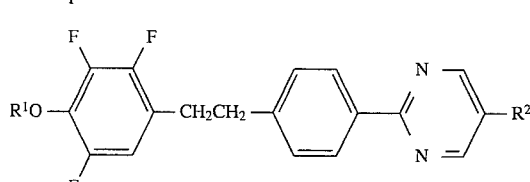
(Ig25)
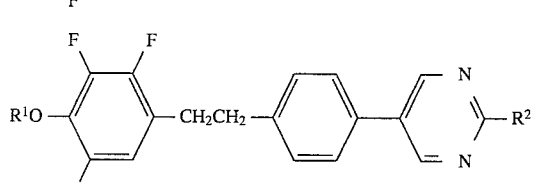
(Ig26)
Preference is furthermore given to the compounds of the sub-structure
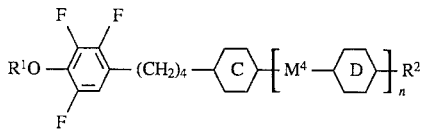
(Ih)
and of these, particular preference is given to the compounds
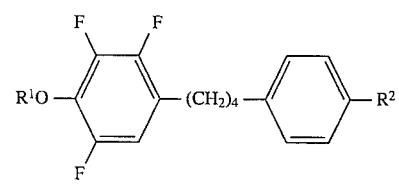
(Ih1)
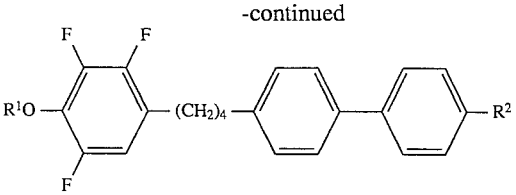
(Ih2)
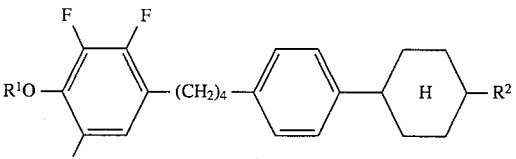
(Ih3)
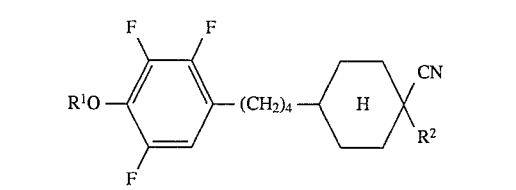
(Ih4)

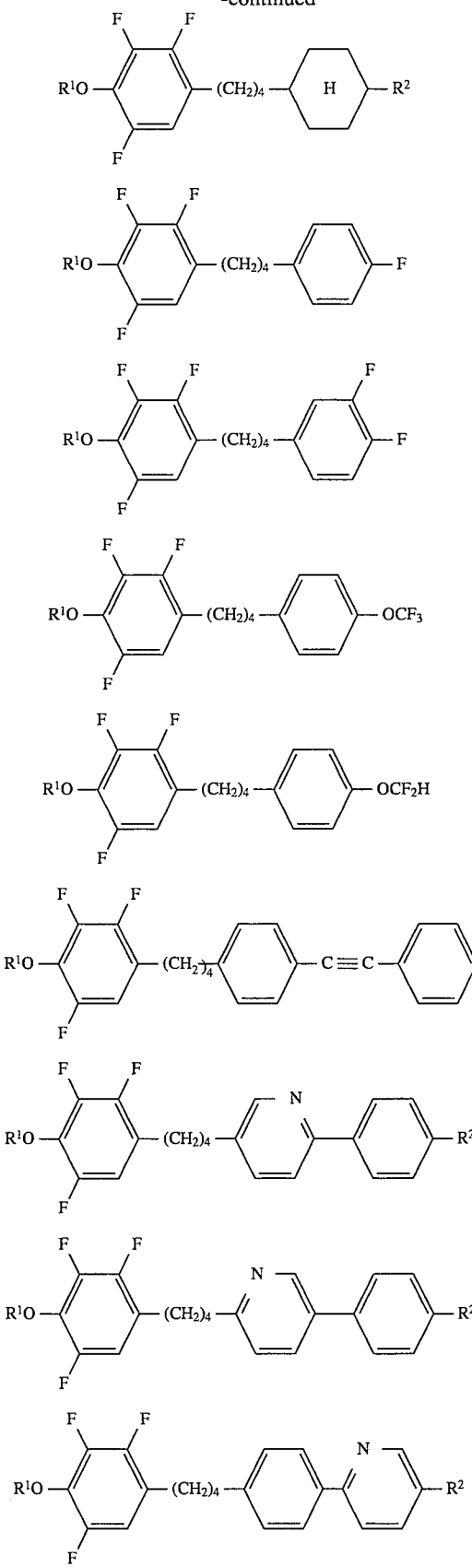
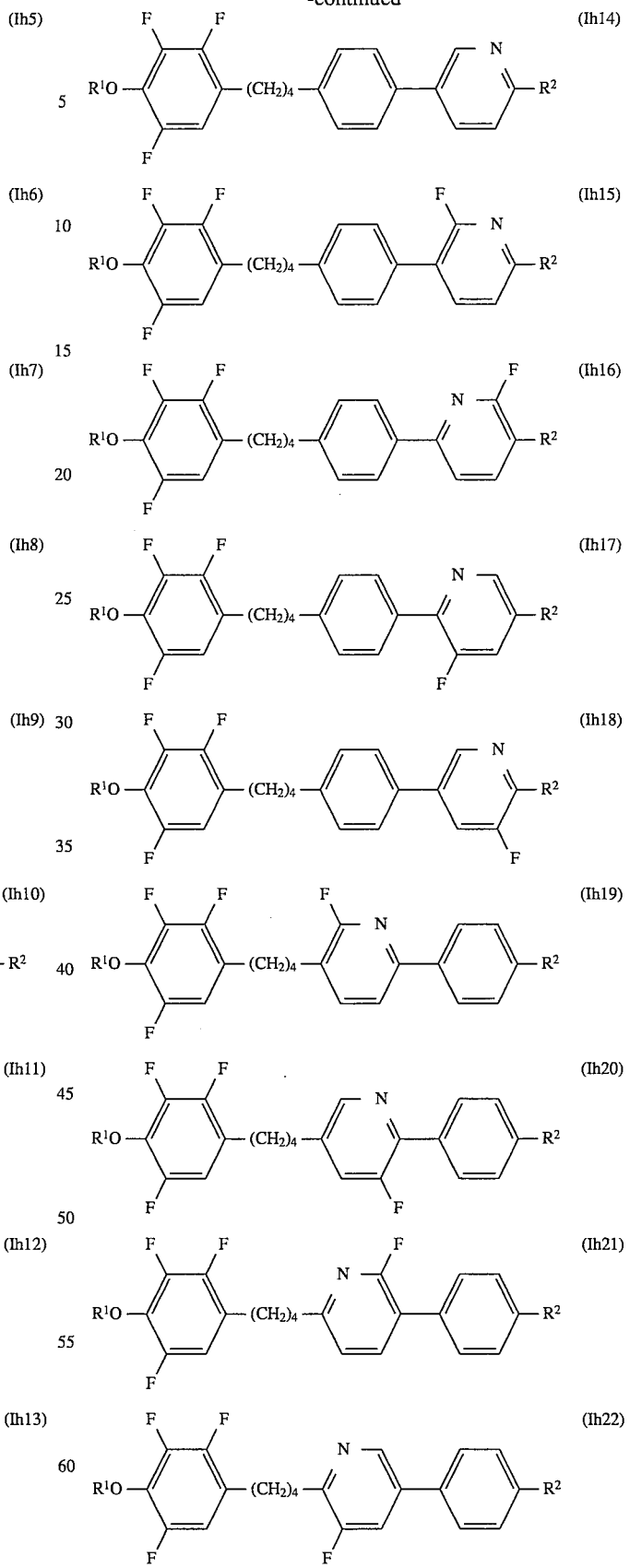

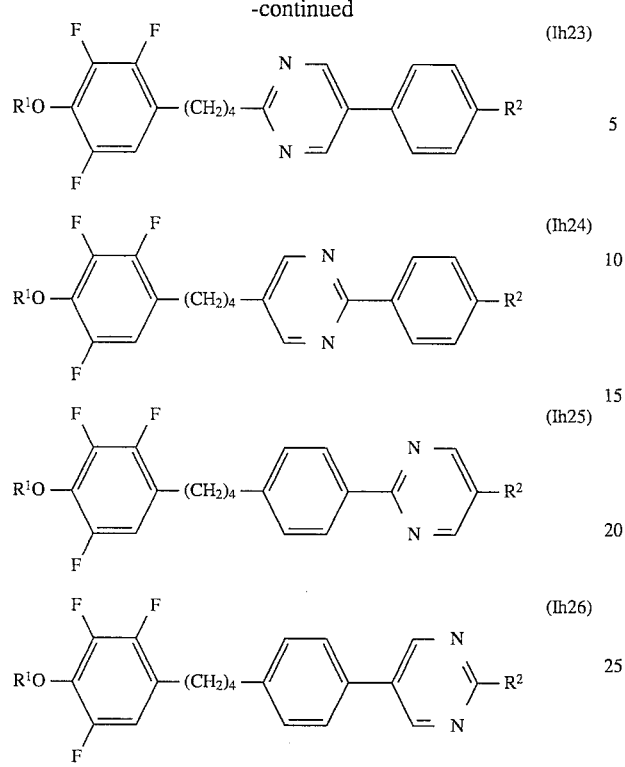
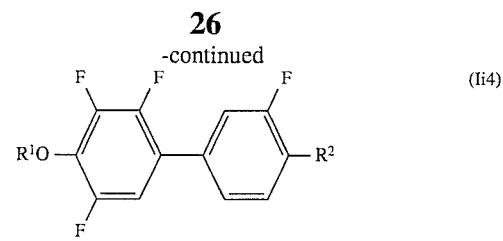
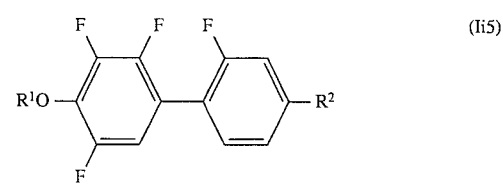
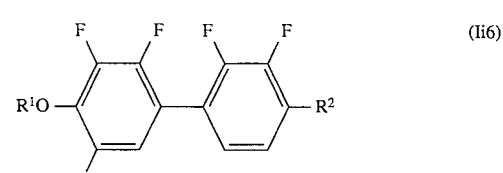
Preference is furthermore given to the compounds of the sub-structure
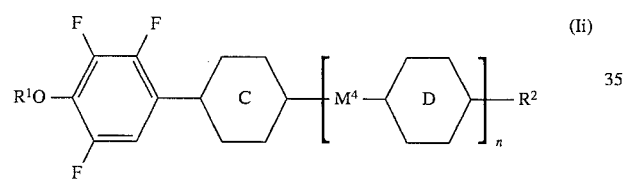
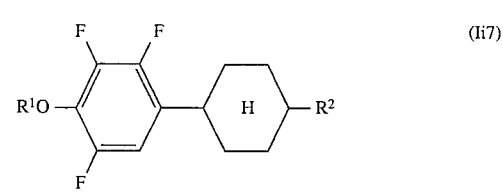
and of these, particular preference is given to the compounds
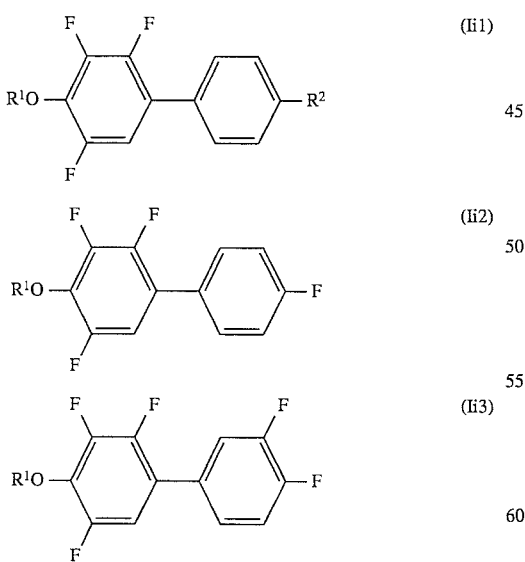
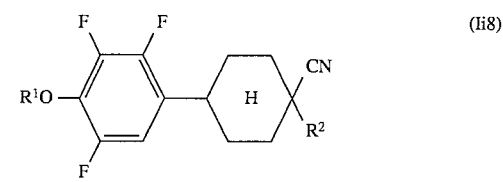
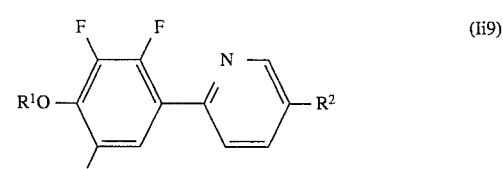
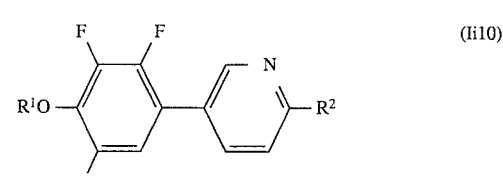
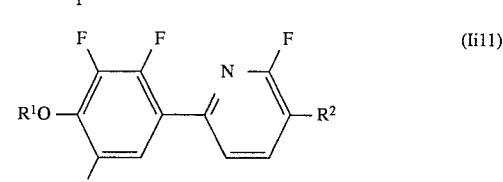
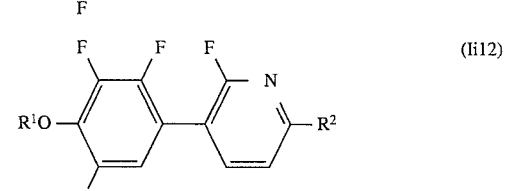

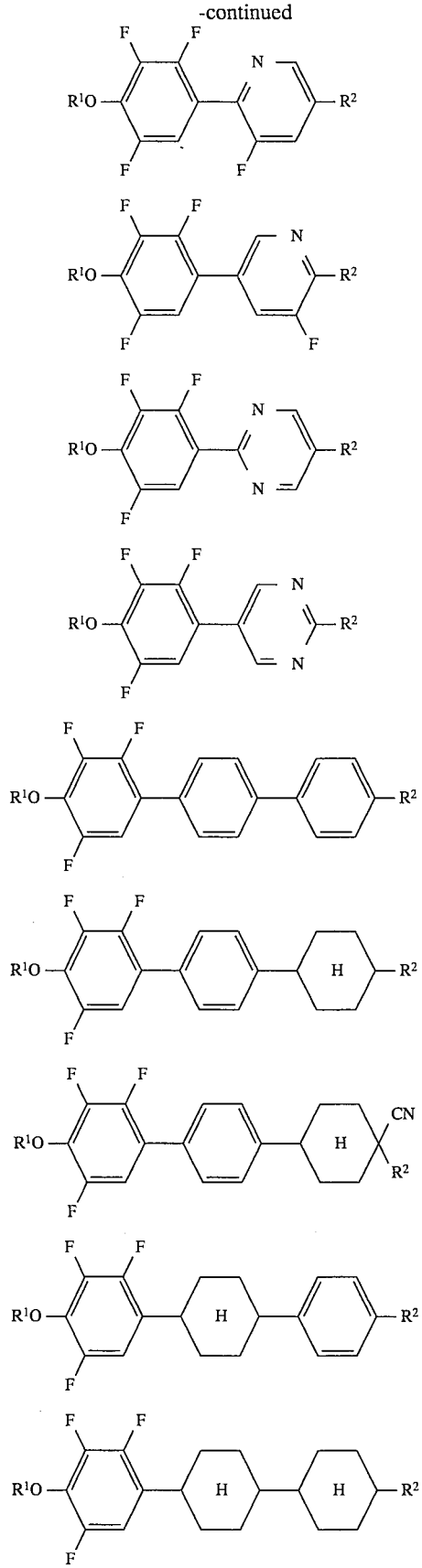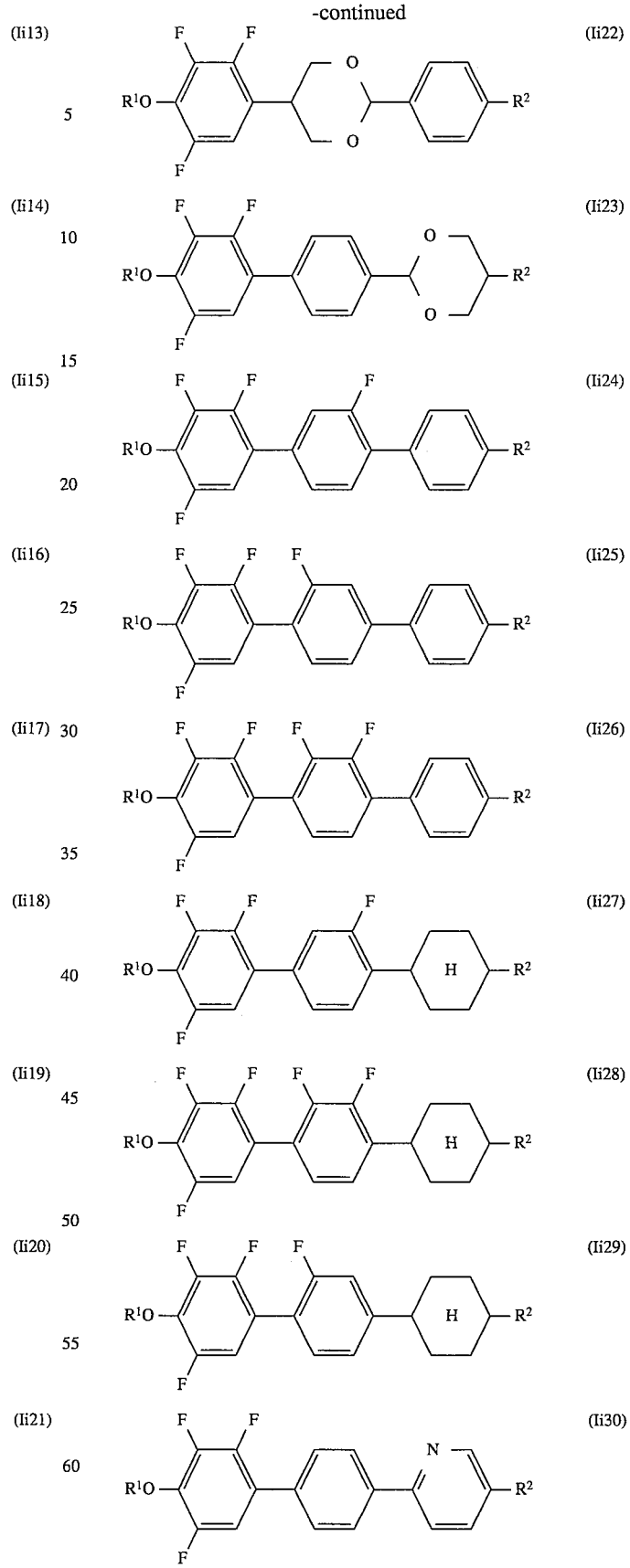

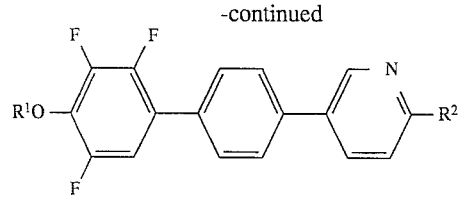
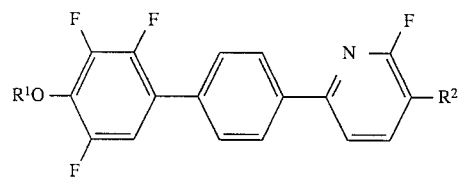
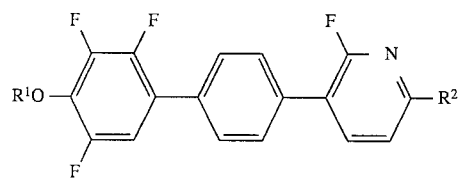
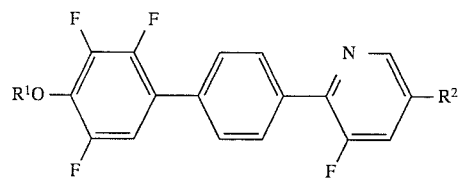
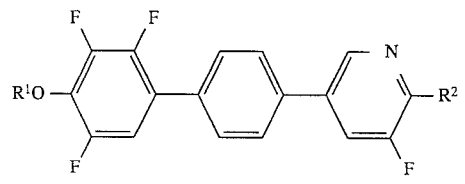
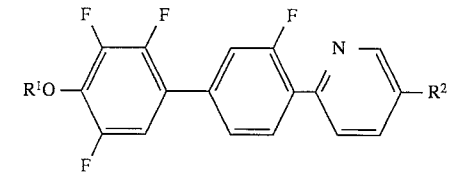
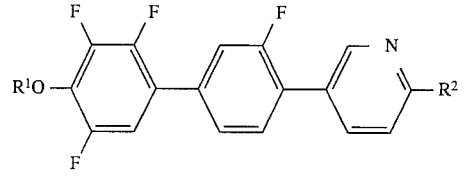
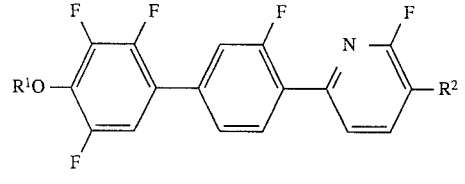
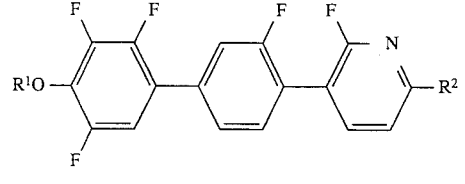

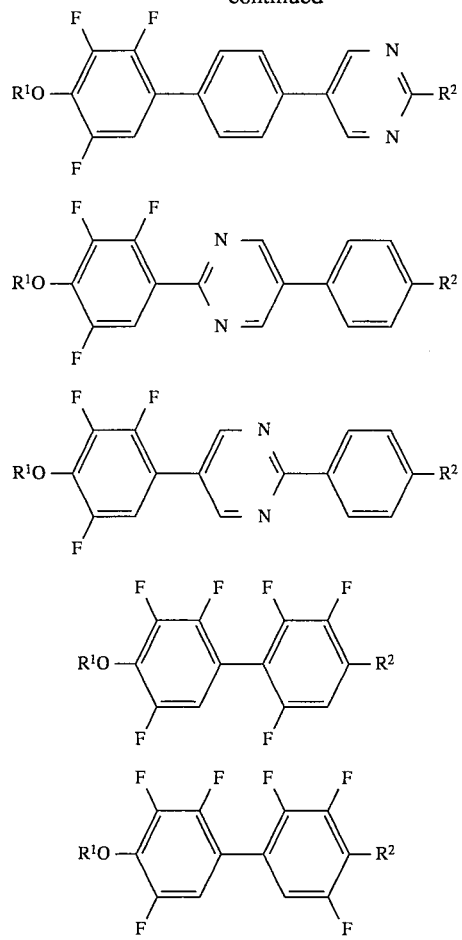

(Ii49)
(Ii50)
(Ii51)
(Ii52)
(Ii53)

Preference is furthermore given to the compounds of the sub-structure

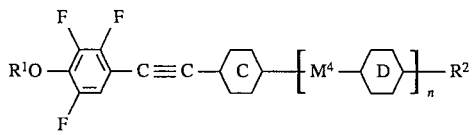

and of these, particular preference is given to the compounds

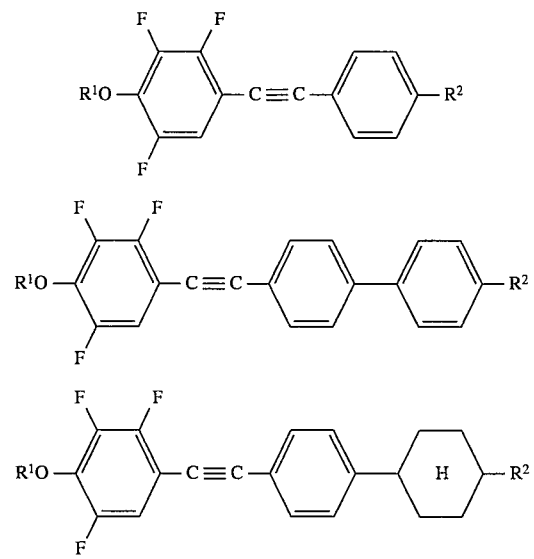

(Ij1)
(Ij2)
(Ij3)

Preference is furthermore given to the compounds of the sub-structure

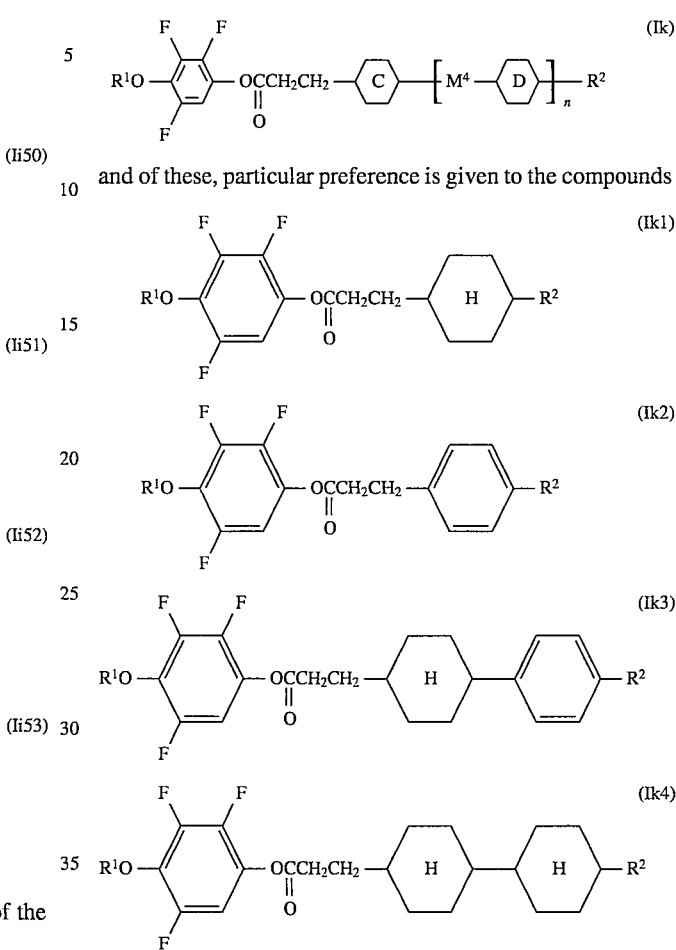

(Ik)
(Ik1)
(Ik2)
(Ik3)
(Ik4)

and of these, particular preference is given to the compounds

Preference is furthermore given to the compounds of the sub-structure

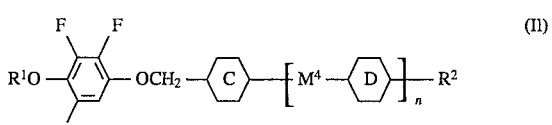

(Il)

and of these, particular preference is given to the compounds

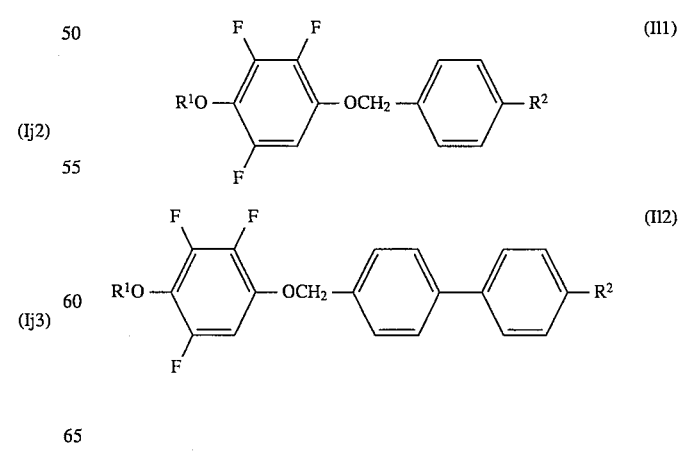

(Il1)
(Il2)

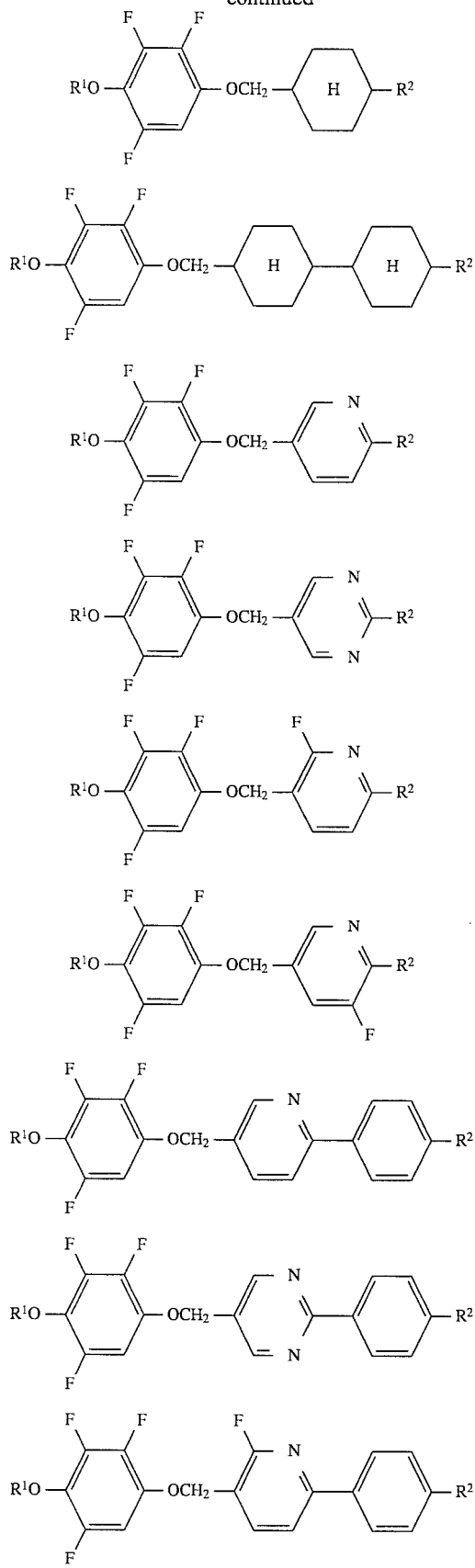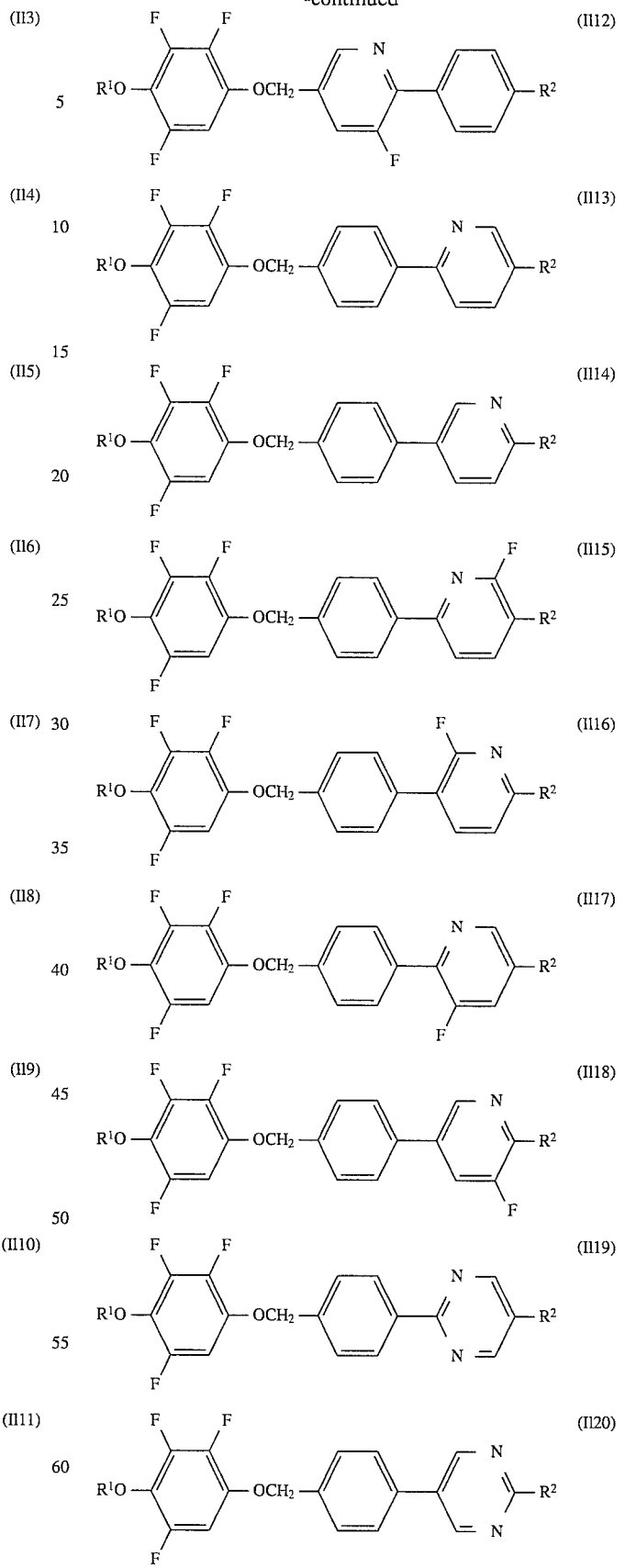

Preference is furthermore given to the compounds of the sub-structure
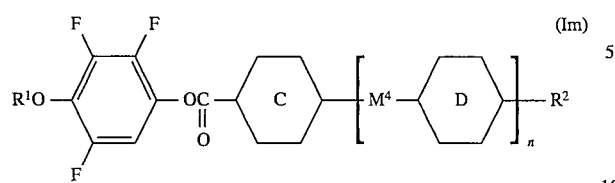
and of these, particular preference is given to the compounds
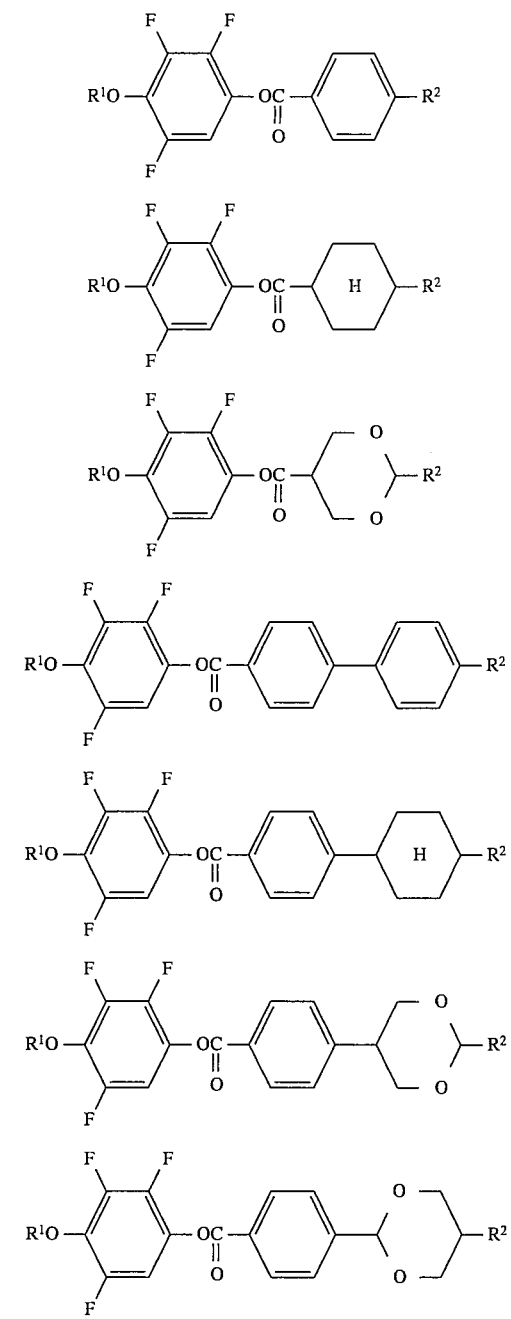
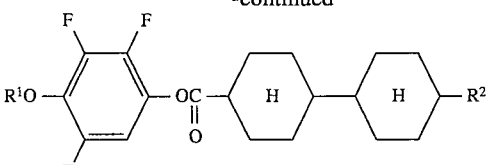
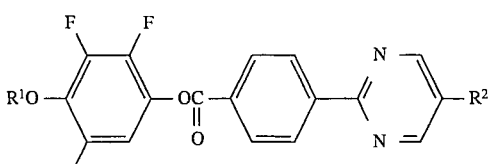

Preference is furthermore given to the compounds of the sub-structure
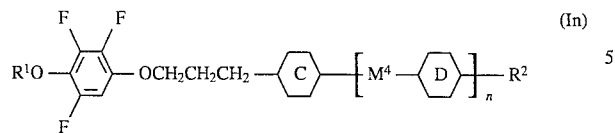
(In)
and of these, particular preference is given to the compounds
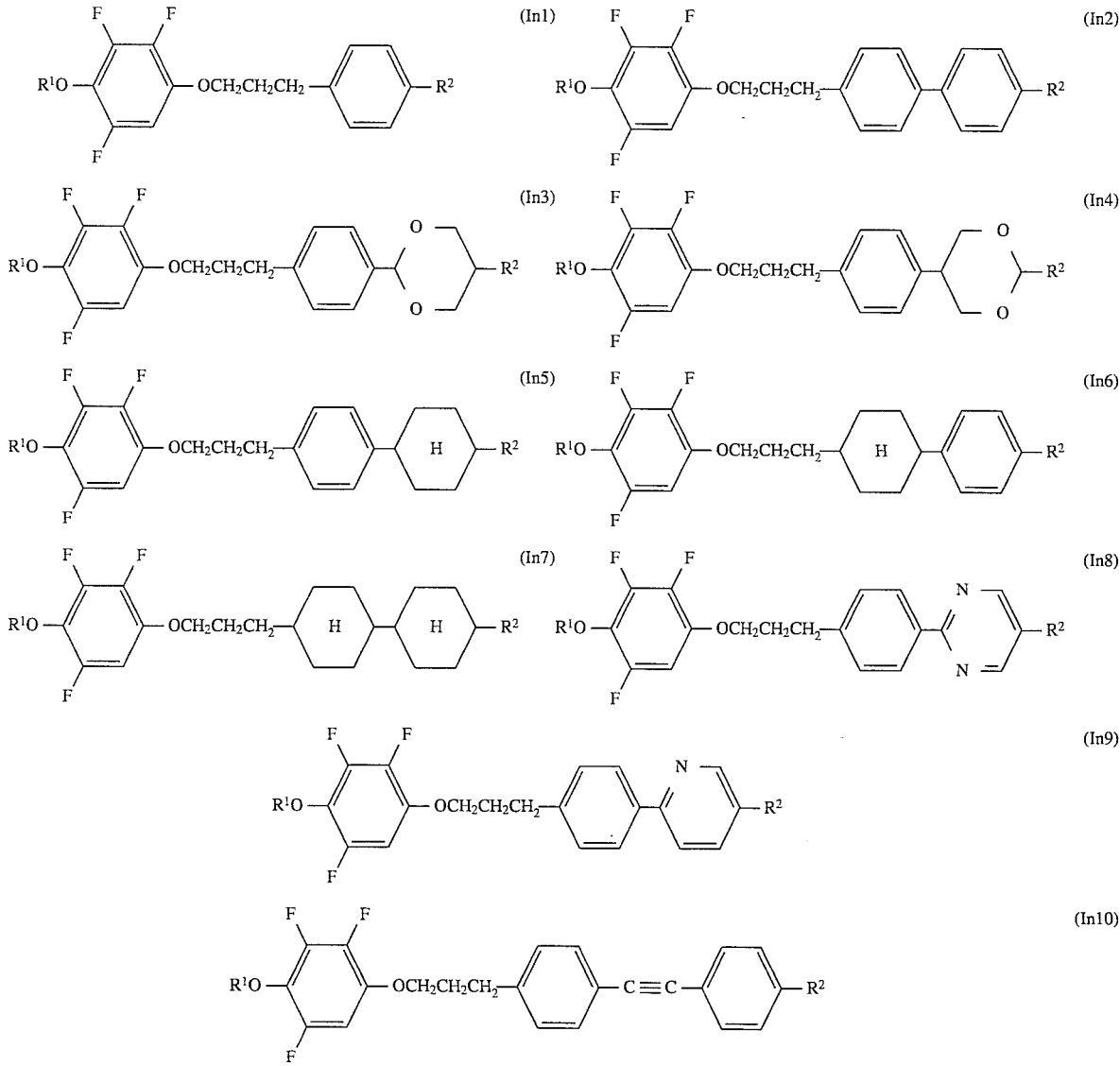
Preference is furthermore given to the compounds of the sub-structure
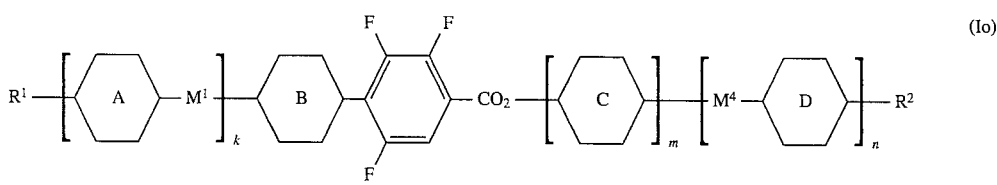
(Io)

and of these, particular preference is given to the compounds
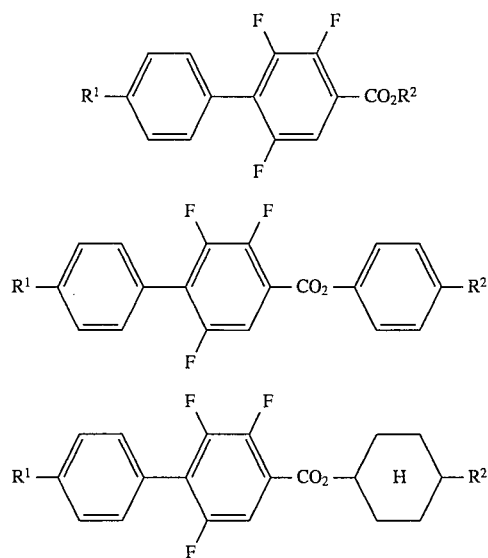
(Io1)
(Io2)
(Io3)
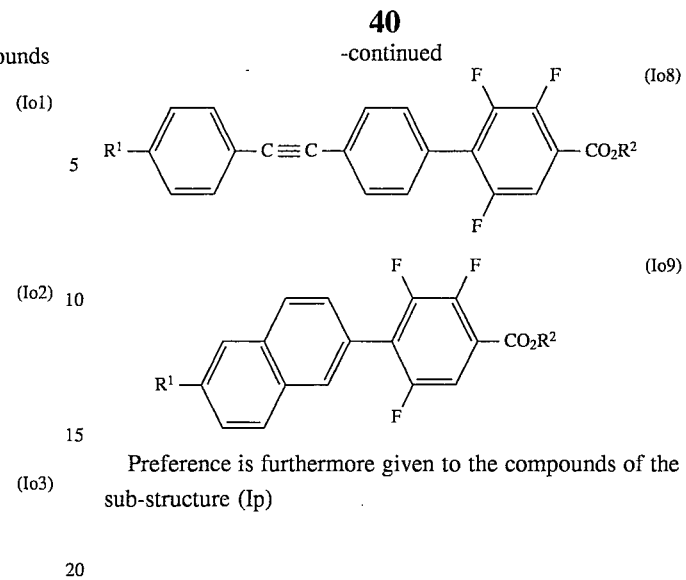
(Io8)
(Io9)
Preference is furthermore given to the compounds of the sub-structure (Ip)
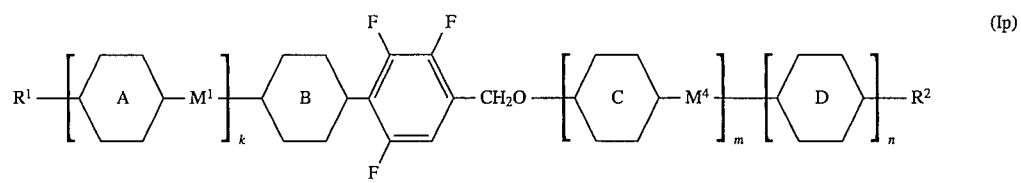
(Ip)
-continued
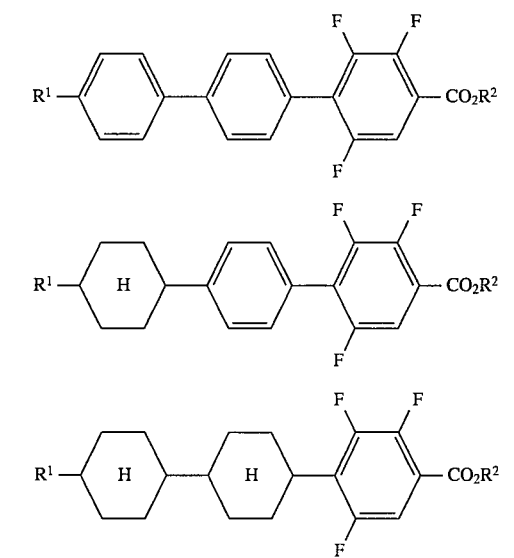
(Io4)
(Io5)
(Io6)
(Io7)
and of these, particular preference is given to the compounds
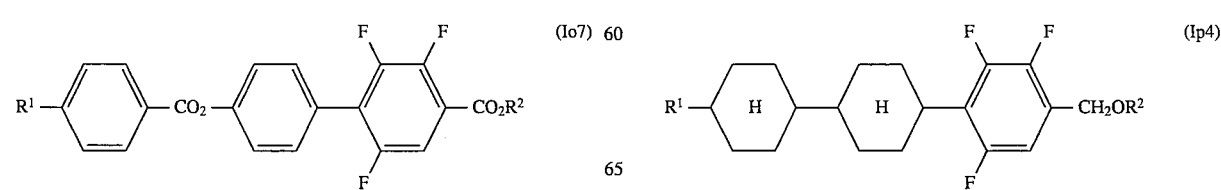
(Ip1)
(Ip2)
(Ip3)
(Ip4)

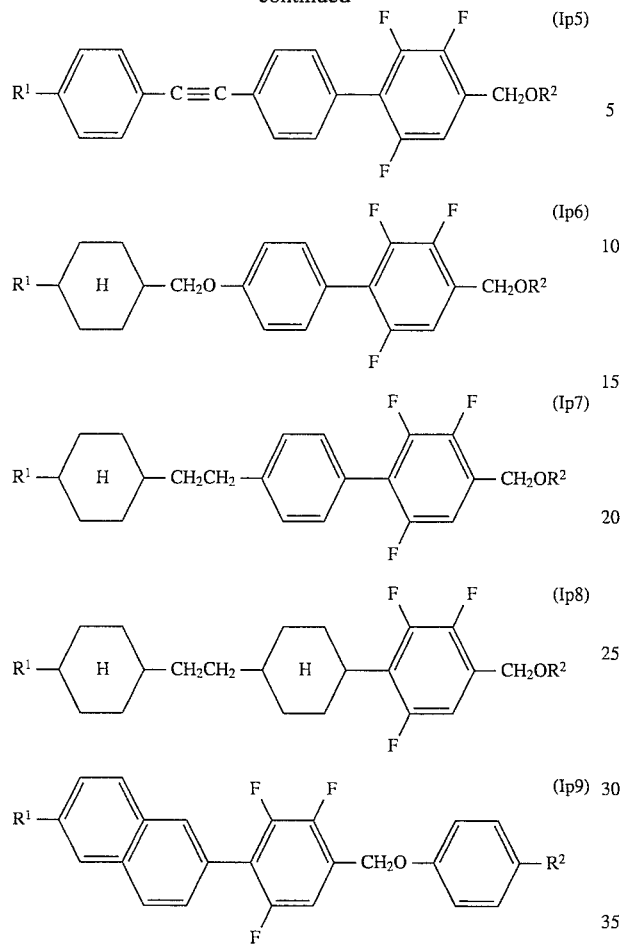
Preference is furthermore given to the compounds of the sub-structure (Iq)
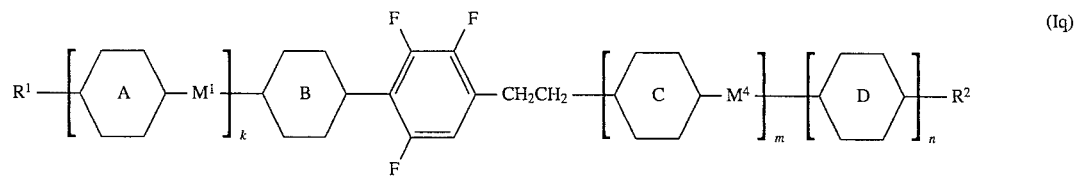
and of these, particular preference is given to the compounds
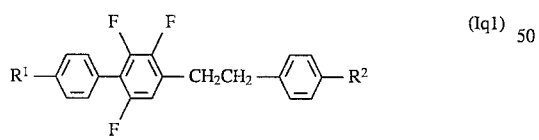
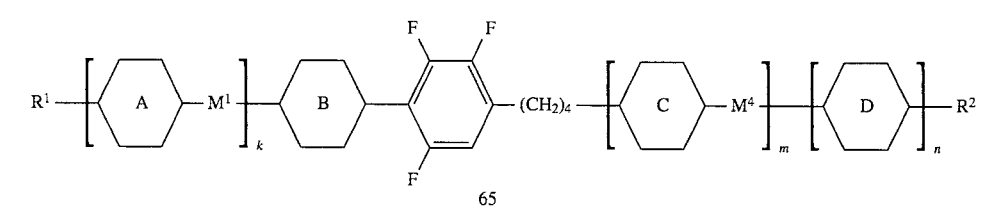

and of these, particular preference is given to the compounds
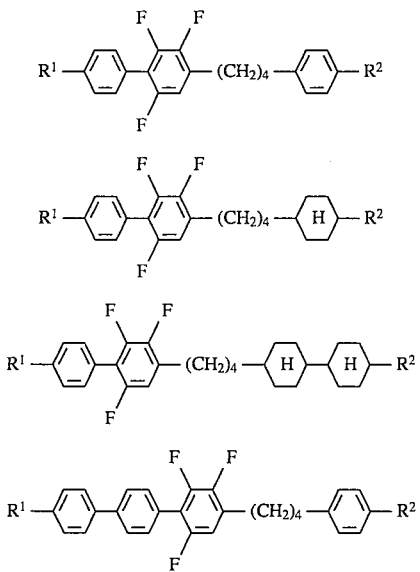
Preference is furthermore given to the compounds of the sub-structure
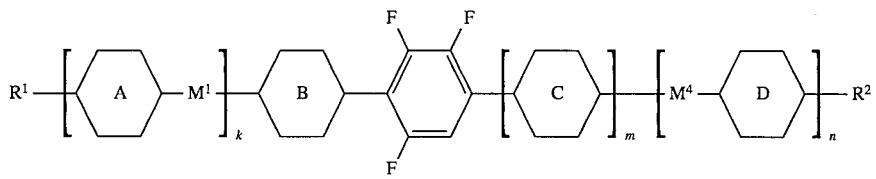
and of these, particular preference is given to the compounds
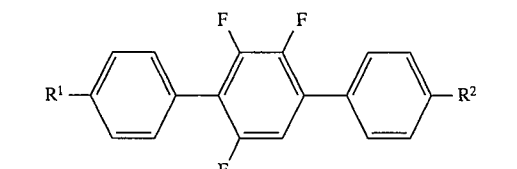
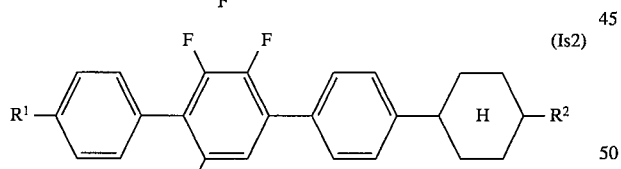
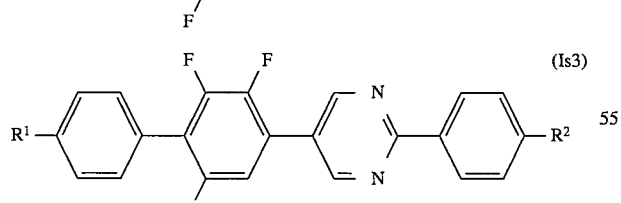
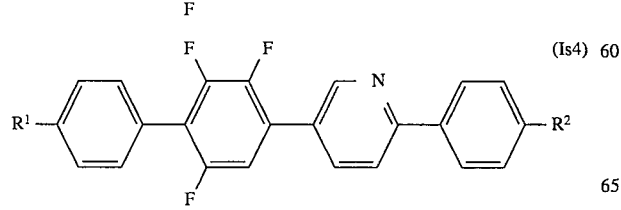
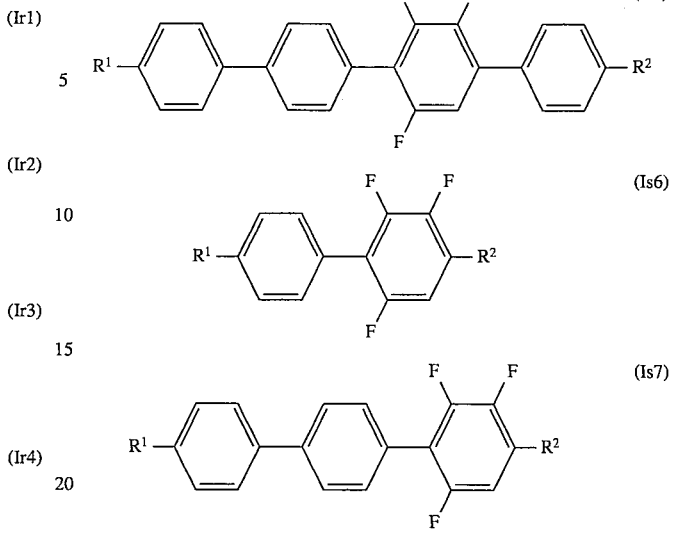
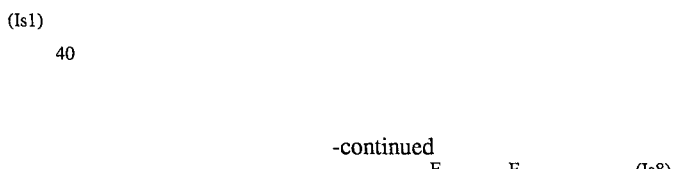
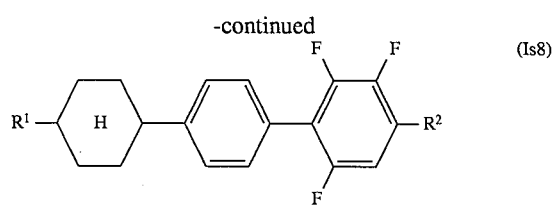
-continued
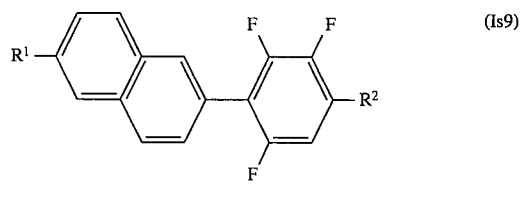
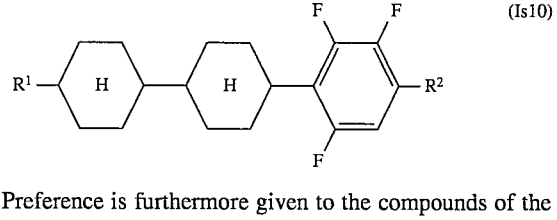
Preference is furthermore given to the compounds of the sub-structure

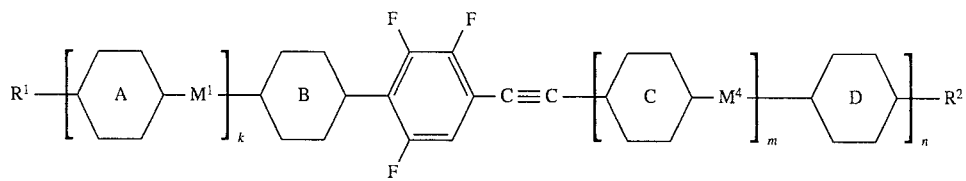
and of these, particular preference is given to the compounds
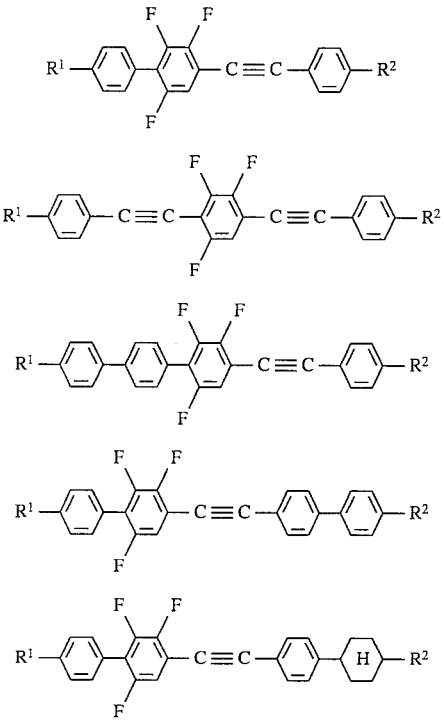
Preference is furthermore given to the compounds of the sub-structure
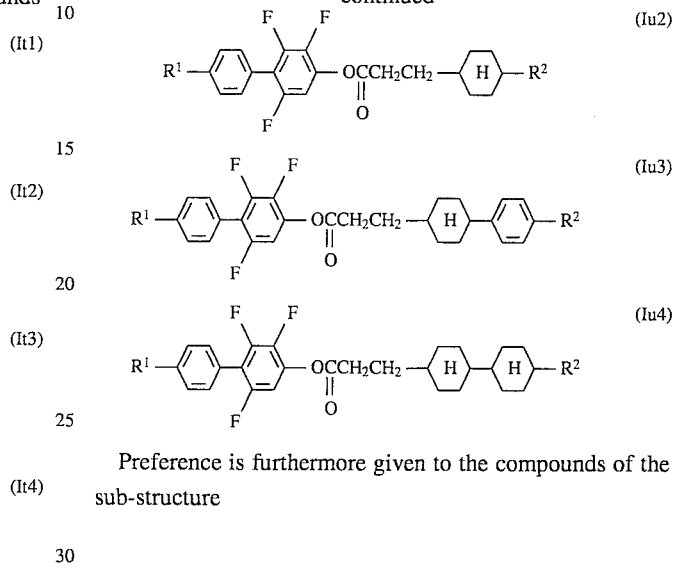
Preference is furthermore given to the compounds of the sub-structure
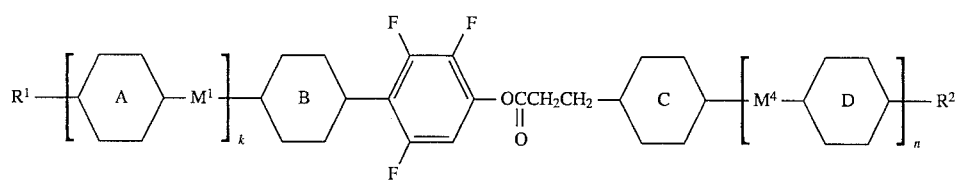
and of these, particular preference is given to the compounds
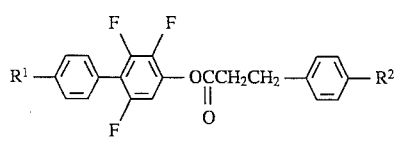
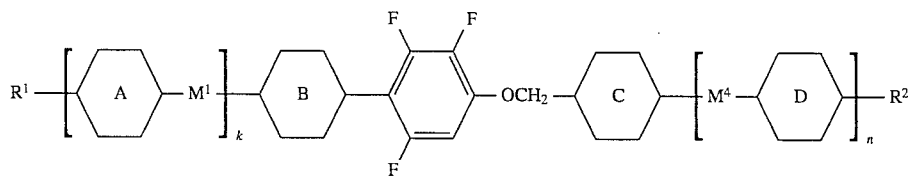

and of these, particular preference is given to the compounds
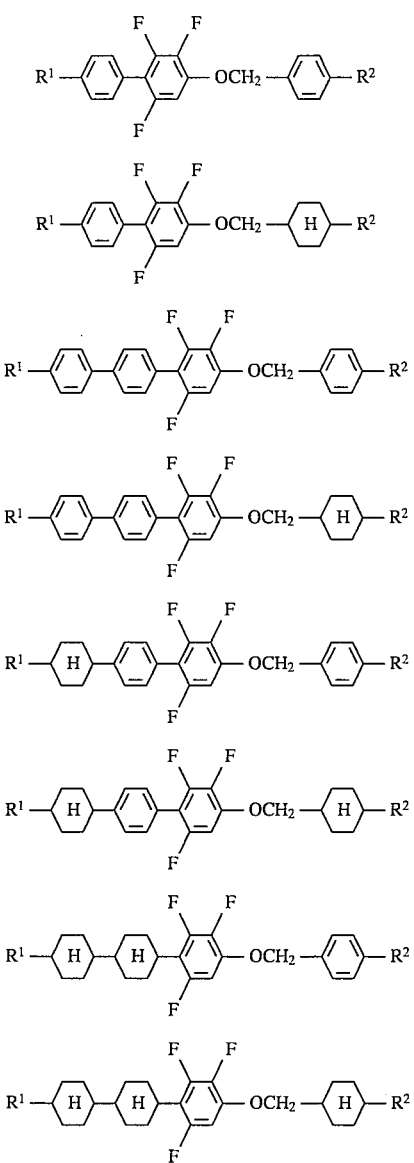
Preference is furthermore given to the compounds of the sub-structure
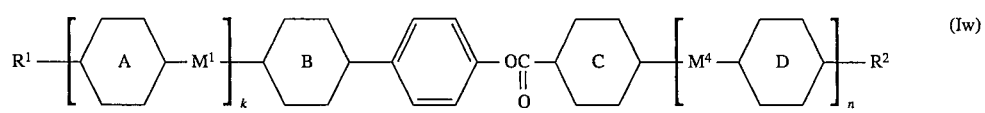
and of these, particular preference is given to the compounds
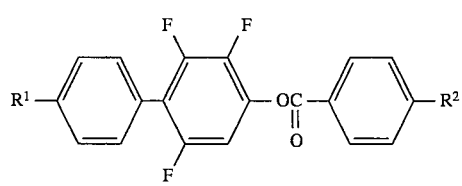
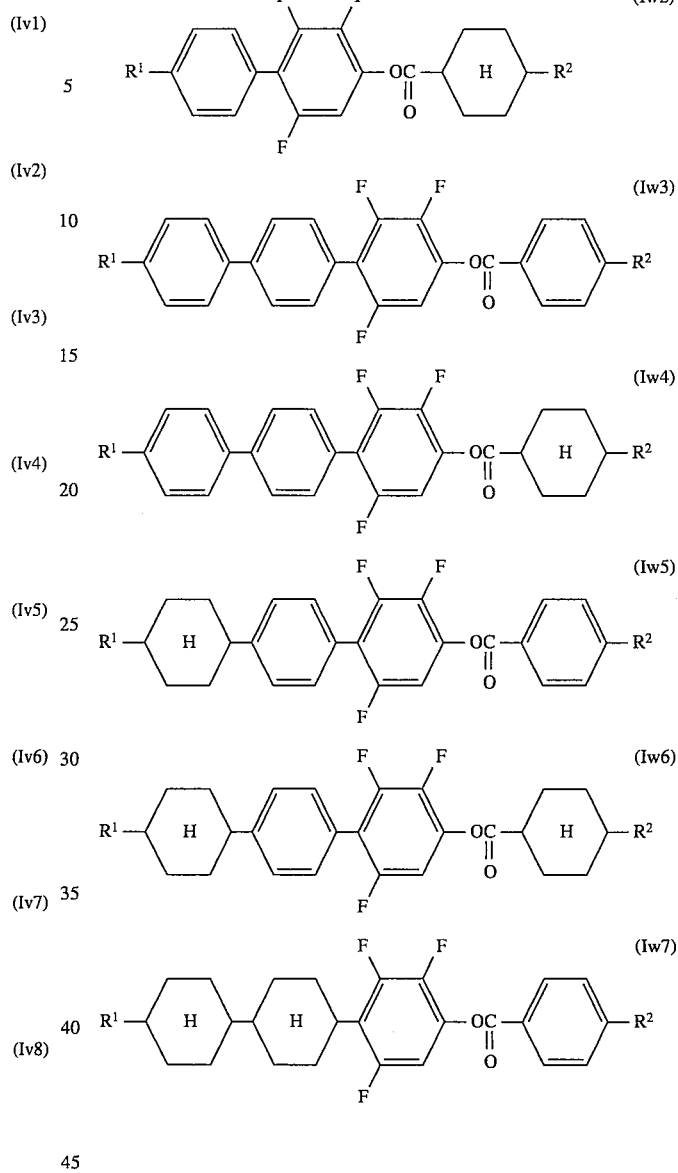
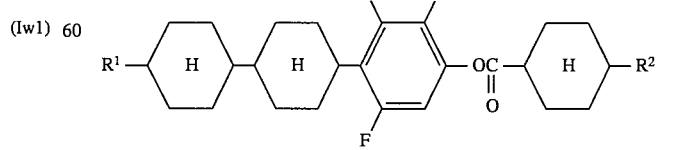
Preference is furthermore given to the compounds of the sub-structure

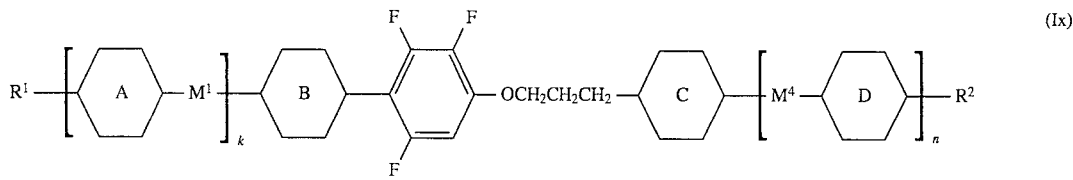

and of these, particular preference is given to the compounds

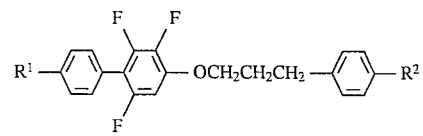

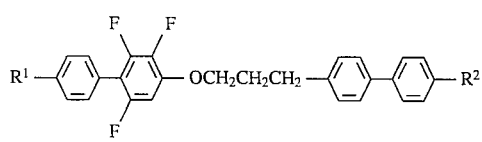

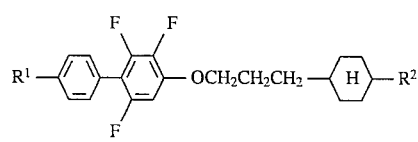

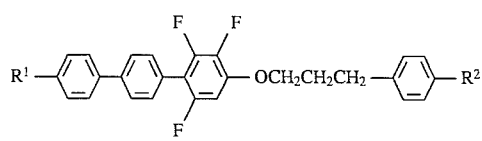

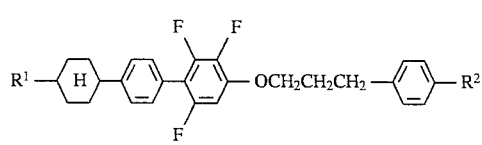

The compounds according to the invention are prepared by methods known per se from the literature, as described in the standard works on organic synthesis, for example Houben-Weyl, Methoden der Organischen Chemie [Methods of Organic Chemistry], Georg-Thieme-Verlag, Stuttgart.

The preparation is carried out under reaction conditions which are known and suitable for said reactions- Use may also be made here of variants which are known per se, but are not mentioned in greater detail here.

For example, as proposed in DE-P 42 42 696.0, bifunctional 4-hydroxy-2,3,5-trifluorobenzoic acid (II) can advantageously be employed as starting material. This is described in greater detail in Schemes 1 to 7.

Scheme 1 describes the synthesis of sub-structures Ia and Ib by reaction of (II) with alkyl derivatives by standard methods (for example R. C. Larock, Comprehensive Organic Transformations, VCH Publishers, New York, p. 445) to give alkyl phenyl ethers, and subsequent reaction thereof with phenols by standard methods (for example R. C. Larock, p. 966) to give the esters Ia and Ib.

By essentially analogous processes, the synthesis of sub-structures Ic and Id is described in Scheme 2, where the first step, for reaction of the carboxyl function with alcohols, can be carried out by standard methods (for example R. C. Larock, p. 966).

Scheme 3 describes the synthesis of benzyl ethers Ie and If, (II) by derivatization of the phenol function, as described in Scheme 1, subsequent reduction of the carboxyl group (for example as described by R. C. Larock, p. 548), and preparation of the benzyl ethers by standard methods (for example T. W. Greene, P. G. M. Wuts, Protective Groups in Organic Synthesis, J. Wiley & Sons, N.Y., 1991, pp. 156–160).

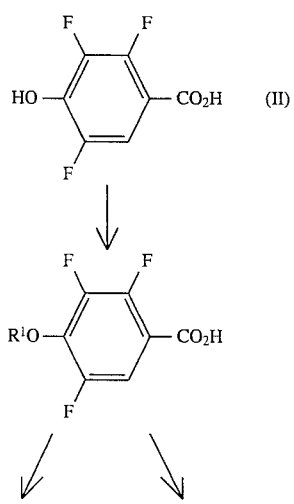

Scheme 1

-continued
Scheme 1
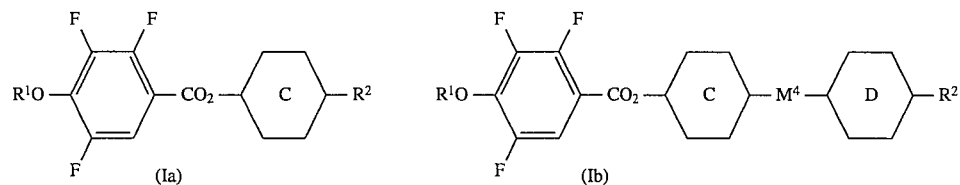
Scheme 2
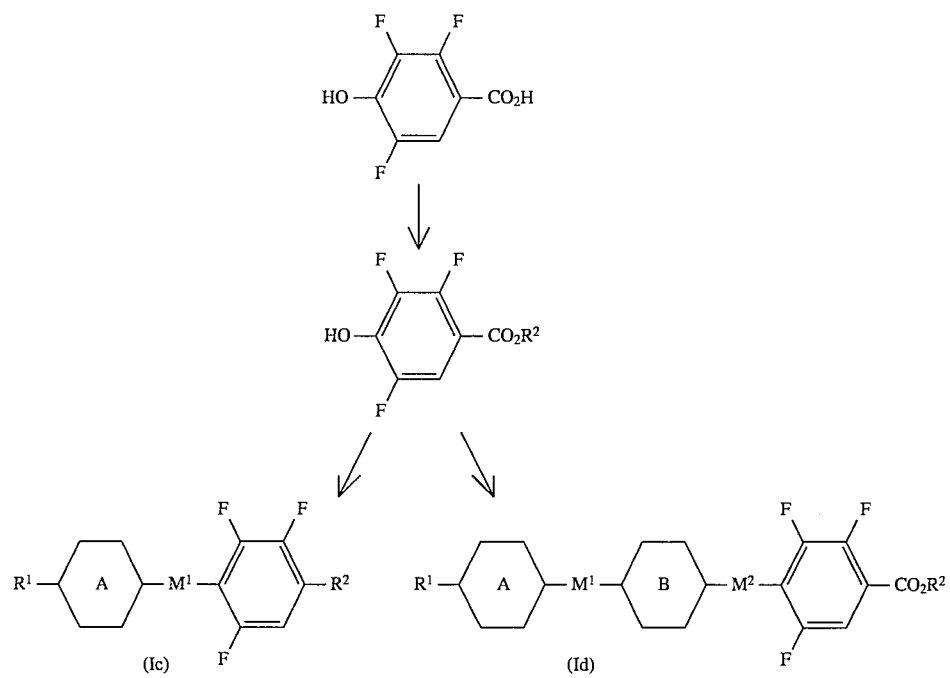
Scheme 3
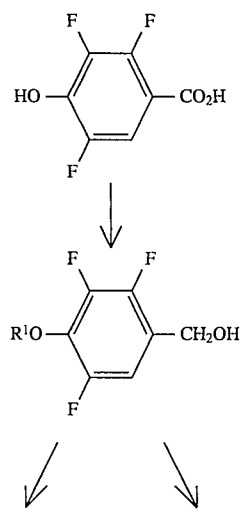

Scheme 3 (continued)

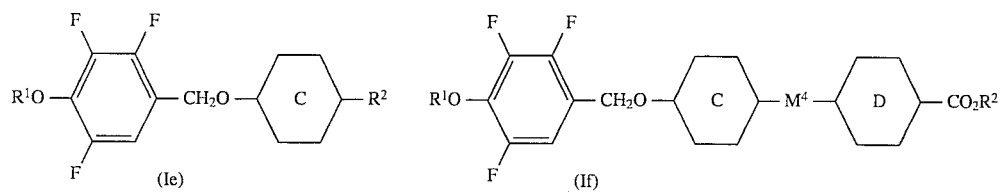

Scheme 4

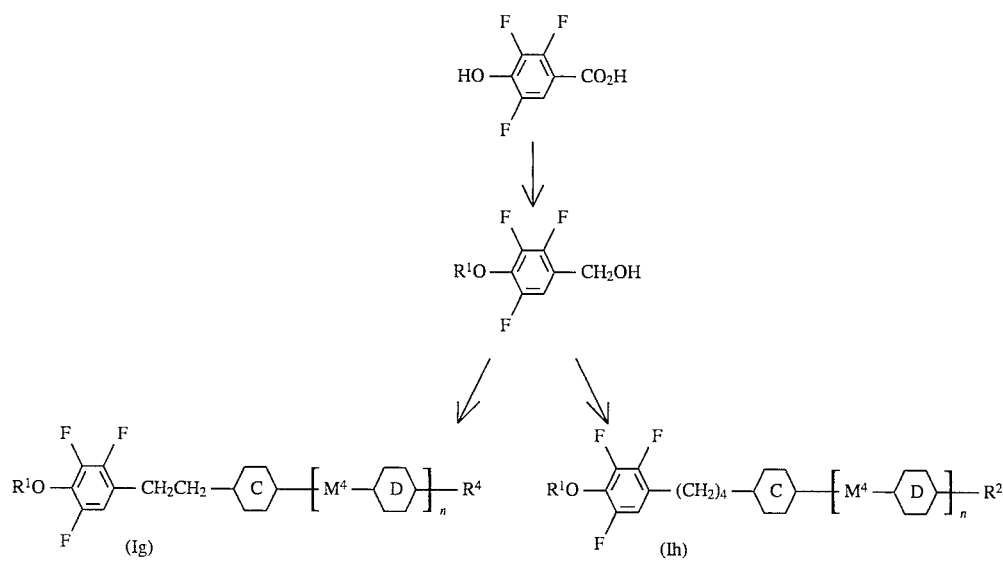

The benzyl alcohols obtained as in Scheme 3 can also be reacted, as described in Scheme 4, after prior conversion into an ester of toluene sulfonic acid, with organometallic compounds to give the alkyl-bridged sub-structures, as described, for example, in DE-A 32 01 721 for comparable compounds.

Scheme 5 describes the synthesis of sub-structures Ii to In. The central precursor is the halogen compound (III), which can be obtained by standard methods (for example R. C. Larock, p. 381) from the carboxylic acid derivatized as in Scheme 1. Standard methods (for example Synthetic Comm. 11 (1981), 513; Tetrahedron Letters 28 (1987), 5093; J. Chem. Soc. Perkin Trans. II 1989, 2041; Mol. Cryst. Liq. Cryst. 172 (1989), 165; DE-C 3930663; EP-A 354434; EP-A 449015; WO 89/03821; WO 89/12039) can be used to react (III) with organometallic compounds or (aryl)boronic acids to give sub-structure (Ii). Sub-structure (Ij) can be obtained analogously to Liq. Crystals 8 (1990), 861.

(III) can also be converted by standard methods (for example R. C. Larock, p. 490) into the phenol (IV) which can itself be converted into sub-structures (Ik), (Il), (Im) and (In) by the methods already described above.

Scheme 5

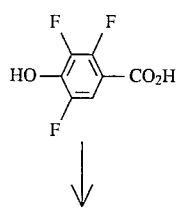

-continued
Scheme 5

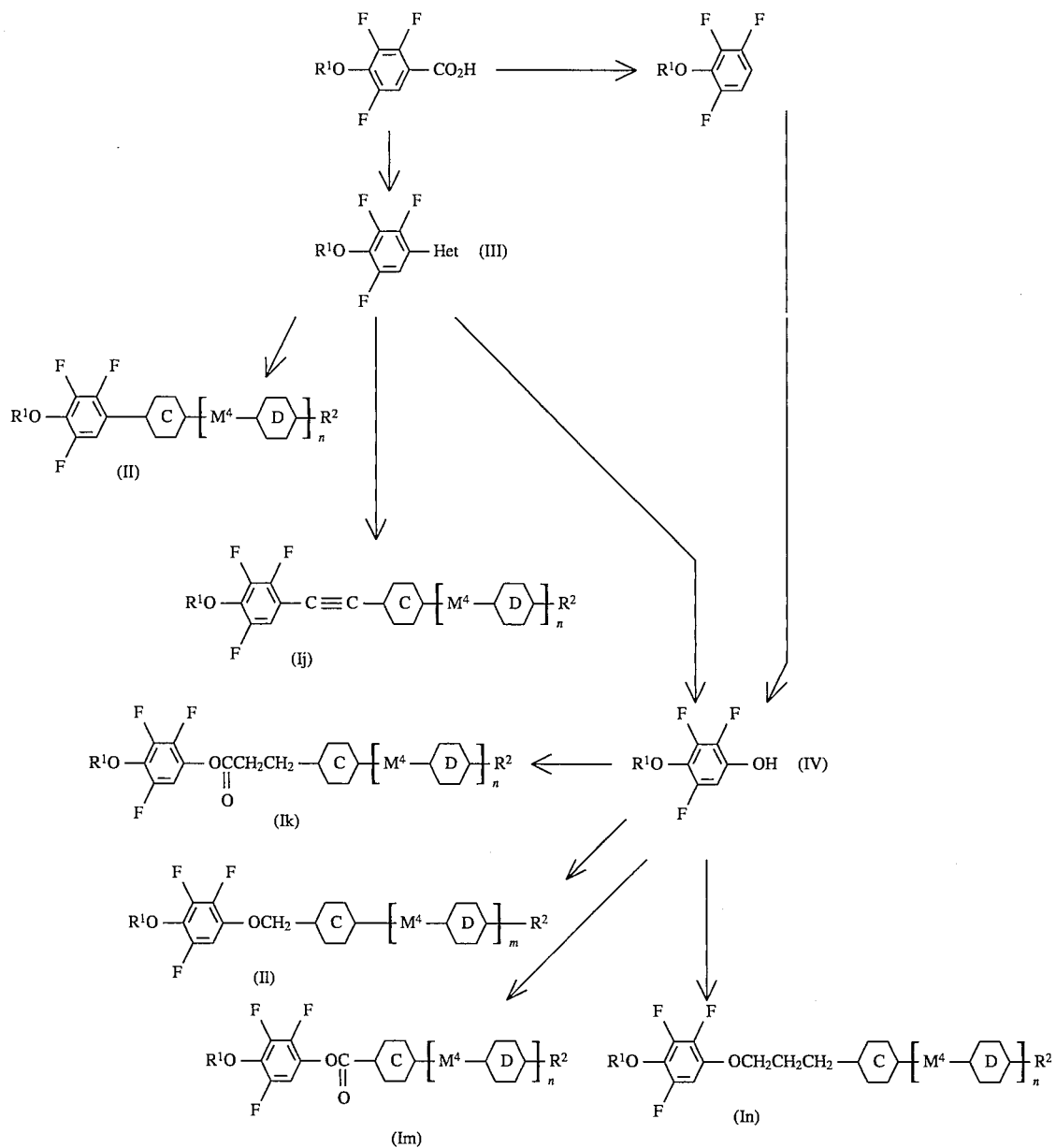

Sub-structures (Io), (Ip), (Iq) and (Ir) in Scheme 6 are likewise derived from (II), which is converted by reaction with perfluoroalkanesulfonic acid derivatives into the ester (V) of the perfluoroalkanesulfonic acid (as described, for example, in J. Org. Chem. 30, 4322 (1965)); the latter can be converted into sub-structures (Io), (Ip), (Iq) and (Ir) by the processes already cited above.

Scheme 7 shows how (V) can be converted into sub-structures (Is) to (Ix) by processes already cited above.

Scheme 6
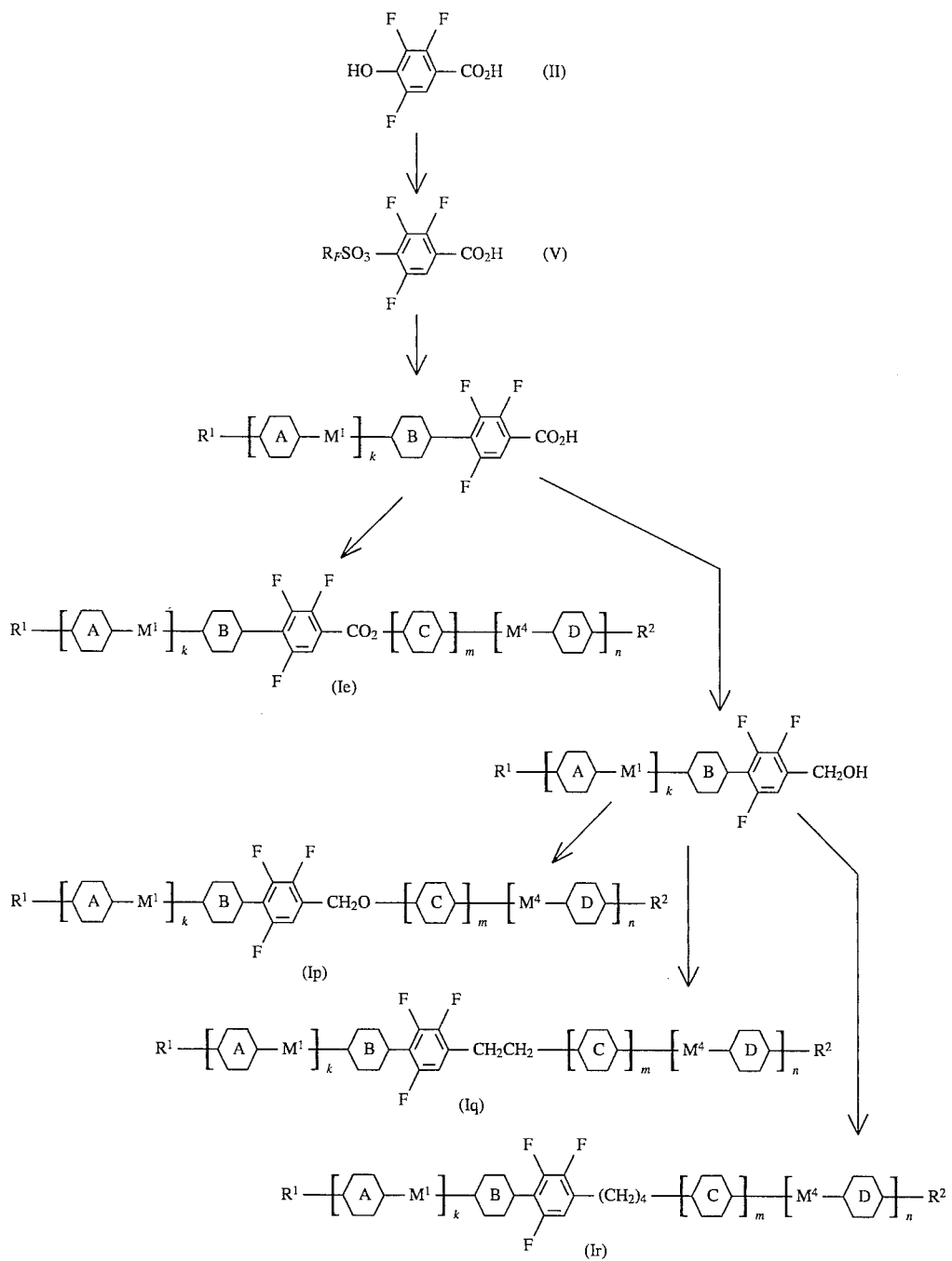

Scheme 7

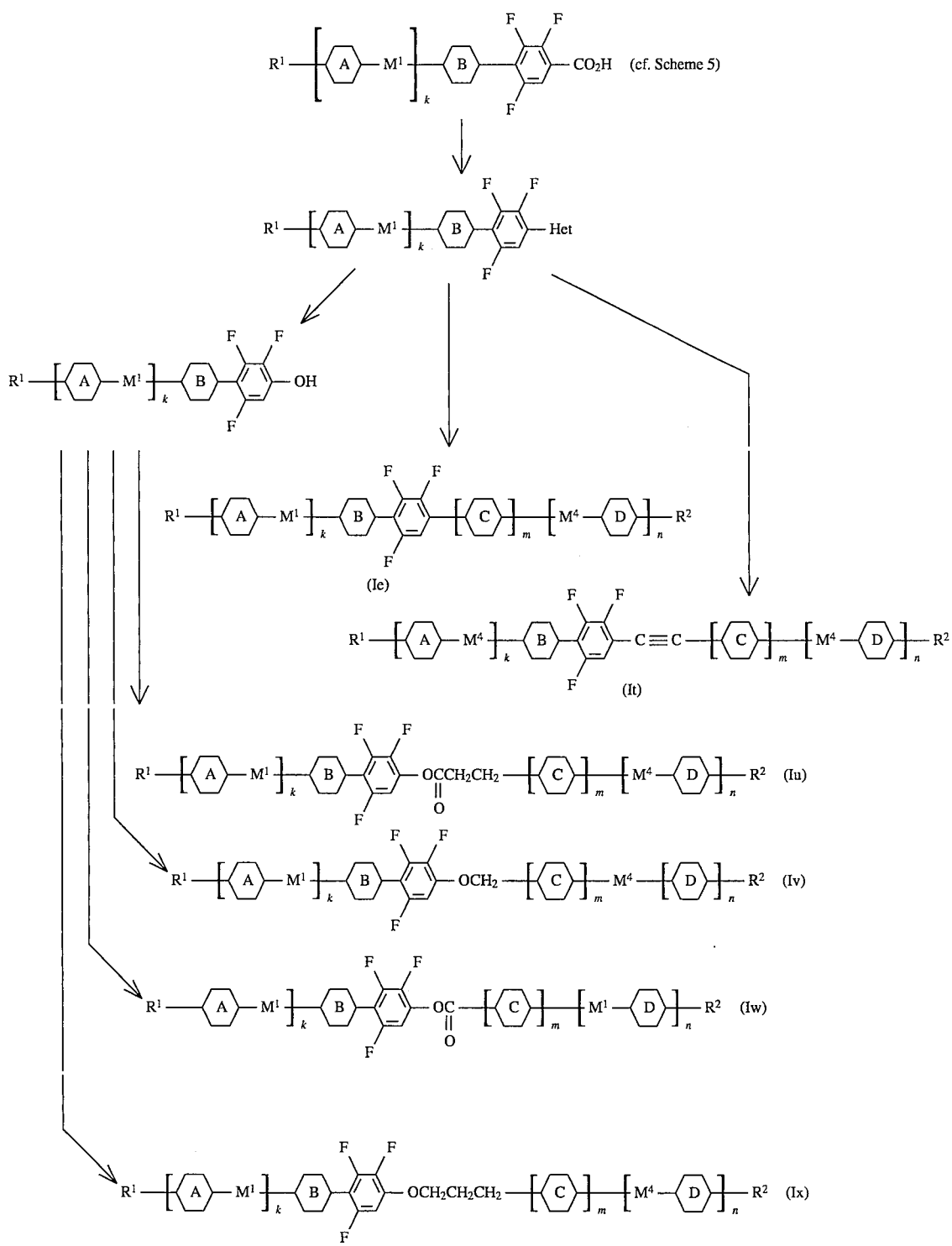

It is of course also possible to use other suitable starting materials for the synthesis of the novel compounds. Thus, for example—analogously to Scheme 3 or 7—commercially available 2,3,5-trifluorobromobenzene can be used (see Example 18). It is also advantageous to use 1,2,4-trifluorobenzene (commercially available)—analogously to, for example, Scheme 5—for the synthesis of the novel compounds.

It desired, the starting materials can also be formed in situ by not isolating them from the reaction mixture, but instead immediately converting them further into the compounds of the formula (I).

Said trifluorophenylene compounds are suitable as components of liquid-crystal (LC) mixtures, preferably those comprising from 2 to 35, particularly preferably 2 to 20, compounds. The LC mixtures here can contain from 0.01 to 80% by weight, preferably from 0.1 to 60% by weight, particularly preferably from 0.1 to 30% by weight, of one or more, preferably from 1 to 10, of the novel compounds.

The other constituents are preferably selected from known compounds having nematic, cholesteric and/or smectic phases; these include, for example, Schiff's bases, biphenyls, terphenyls, phenylcyclohexanes, cyclohexylbiphenyls, N-, S- or O-containing heterocyclic compounds, for example pyrimidines, cinnamic esters, cholesterol esters or various bridged, polycyclic esters of p-alkylbenzoic acids with terminal polar groups. Preference is given to the use in ferroelectric and nematic LC mixtures, very particularly preferably in ferroelectric LC mixtures.

The compounds of the formula I have a broad range of applications. Depending on the choice of substituents, these compounds can be used as base materials from which liquid-crystalline, smectic, in particular ferroelectric, phases are predominantly composed; however, it is also possible to add compounds of the formula I to liquid-crystalline base materials from other classes of compounds in order, for example, to vary the dielectric and/or optical anisotropy and/or the viscosity and/or the spontaneous polarization and/or the phase ranges and/or the tilt angle and/or the pitch of a dielectric of this type.

The novel mixtures can in turn be used in electro-optical or fully optical elements, for example display elements, switching elements, light modulators, elements for image processing and/or signal processing or generally in the area of nonlinear optics.

Electro-optical display elements whose liquid-crystalline mixtures contain compounds of the formula I additionally contain, for example, the following components: two electrodes, two outer plates and at least one alignment layer. In general, the structure of FLC displays is described, for example, in EP-B 0 032 362.

A further aspect of the invention is a process for preparing an electrooptical switching and/or display element which comprises filling a liquid-crystalline mixture as described above with spacers between two glass substrates being provided with electrodes and one or two orientation layers.

The present invention is described in greater detail with reference to the examples below.

EXAMPLE 1

4-(1-Methoxycarbonyl)-2,3,5-trifluorophenyl 4-(trans-4-pentylcyclohexyl)benzoate A solution of 2.3 g of methyl 4-hydroxy-2,3,5-trifluorobenzoic acid (prepared by reaction of 4-hydroxy-2,3,5-trifluorobenzoic acid with methanol using N,N'-carbonyldiimidazole; melting point 112°–114° C.) in 40 ml of dichloromethane is treated with 2.3 g of dicyclohexylcarbodiimide and 3.1 g of 4-(trans-4-pentylcyclohexyl)benzoic acid, and the mixture is stirred at 20° C. for 24 hours. After filtration, the mixture is chromatographed on silica gel using dichloromethane/ethyl acetate 4:1. Recrystallization from acetonitrile gives 2.5 g of the product in the form of colorless crystals.

Phase sequence: $X_1$ 60 $X_2$ 68N 176 I

The following are prepared analogously:

EXAMPLE 2

4-(1-Hexyloxycarbonyl)-2,3,5-trifluorophenyl 4-(2,3-difluoro-4-octyloxy)benzoate Phase sequence: X 62 I

EXAMPLE 3

4-(1-Methoxycarbonyl)-2,3,5-trifluorophenyl 4-(2,2,3,3-H-perfluorooctyloxy)benzoate Phase sequence: $X_1$ 71 $X_2$ 99 $S_A$ 106 I

EXAMPLE 4

4-(1-Methoxycarbonyl)-2,3,5-trifluorophenyl 2-(6decyloxy)naphthoate

Phase sequence: $X_1$ 86 $X_2$ 91N 92 I

EXAMPLE 5

4-(1-Methoxycarbonyl)-2,3,5-trifluorophenyl 4-(4'-octyloxy-1,1'-biphenyl)carboxylate Phase sequence: X 107 $S_A$ 138N 179 I

EXAMPLE 6

4-(1-Methoxycarbonyl)-2,3,5-trifluorophenyl 3-(trans-4-ethylcyclohexyl)propionate Phase sequence: X 22 I

EXAMPLE 7

4-(1-Methoxycarbonyl)-2,3,5-trifluorophenyl 4-(4'-propyl-1,1'-biphenyl)carboxylate Phase sequence: X 105N 172 I

EXAMPLE 8

4-(1-Methoxycarbonyl)-2,3,5-trifluorophenyl 4-(4-decyloxybenzoyloxy)benzoate

Phase sequence: X 119 (74 $S_A$ 107) N 174 I

EXAMPLE 9

Octyl 4-(4-octyloxybenzoyloxy)-2,3,5-trifluorobenzoate

Phase sequence: X 38 I

EXAMPLE 10

Octyl 4-[4-(1,1,2,2-H-perfluorooctyloxy)benzoyl]-2,3,5-trifluorobenzoate

Phase sequence: X 74 (54) $S_c$ (61) $S_A$ (62) I

EXAMPLE 11

1,1,2,2-H-Perfluorooctyl 4-[4-(1,1,2,2-H-perfluoro-octyloxy)benzoyl]-2,3,5-trifluorobenzoate Phase sequence: X 95 $S_c$ 96 $S_A$ 105 I

EXAMPLE 12

4-[1-(1,1,2,2-H-Perfluorooctyloxy)carbonyl]-2,3,5-trifluorophenyl 4-(trans-4-pentylcyclohexyl)benzoate Phase sequence: X 85 $S_A$ 150 I

EXAMPLE 13

4-(1-Butoxycarbonyl)-2,3,5-trifluorophenyl 4-(5-octyl-pyrimidin-2-yl)phenoxyacetate Phase sequence: X 89 I

EXAMPLE 14

Butyl 4-(4-butyldimethylsilylbutoxy)benzoyloxy-2,3,5-trifluorobenzoate

Phase sequence: X -6 I

The following are prepared analogously to Example 1, but using 4-methoxy-2,3,5-trifluorobenzoic acid (prepared by reaction of 4-hydroxy-2,3,5-trifluorobenzoic acid with 2 equivalents of methanol and 2 equivalents of "Mitsunobu reagent" and subsequent hydrolysis of the methyl ester; melting point 142°–145° C.:

EXAMPLE 15

4-(5-Octyloxypyrimidin-2-yl)phenyl 4-methoxy-2,3,5-trifluorobenzoate

Phase sequence: X 117 ($S_A$ 98) N 149 I

EXAMPLE 16

4-(1-Methoxycarbonyl)-2,3,5-trifluorophenyl 4-methoxy-2,3,5-trifluorobenzoate

EXAMPLE 17

4-[1-(1,1,2,2-H-perfluorodecyl)oxycarbonyl]-2,3,5-tri-fluorophenyl 4-methoxy-2,3,5-trifluorobenzoate

EXAMPLE 18

4,4''-bisoctyloxy-2',3',5'-trifluoro-1,1':4',1-terphenyl

A solution of 3.3 g of 4-bromo-2,3,5-trifluoro-4'-octyloxybiphenyl (obtained by Pd-catalyzed reaction of commercially available 2,3,5-trifluorobromobenzene with 4-octyloxyphenylboronic acid to give 4-octyloxy-2',3',5'-trifluorobiphenyl [melting point 31° C.], conversion thereof into the corresponding boronic acid by the sequence lithiation—reaction with trimethyl borate—hydrolysis and finally reaction of the boronic acid with Br$_2$), 4.0 g of 4-octyloxyphenylboronic acid, 0.1 g of tetrakis(triphenylphosphine)palladium(0) and 5.1 g of Na$_2$CO$_3$ in 90 ml of toluene, 45ml of ethanol and 30 ml of H$_2$O is heated at the boil for 2 hours. Conventional work-up, purification by chromatography and recrystallization from acetonitrile give the product.

Phase sequence: X 98 N 110 I

Use Example 1

An $S_c$ base mixture having a melting point of +4° C. and a clearing point of 85° C. and having the composition [mol %]

| | |
|---|---|
| 5-octyl-2-(4-hexyloxyphenyl)pyrimidine | 21.45% |
| 5-octyl-2-(4-decyloxyphenyl)pyrimidine | 14.30% |
| 5-octyl-2-(4-octyloxyphenyl)pyrimidine | 19.25% |
| 5-octyloxy-2-(4-hexyloxyphenyl)pyrimidine | 13.40% |
| 5-octyloxy-2-(4-octyloxyphenyl)pyrimidine | 6.20% |
| 5-octyloxy-2-(4-butyloxyphenyl)pyrimidine | 14.15% |
| 5-octyloxy-2-(4-decyloxyphenyl)pyrimidine | 11.25% | is treated with 10 mol % of the compound from Example 1; the melting point is lowered by 5K to −1° C., while the somewhat undesired reduction in the clearing point by 2K to 83° C. is small. This example confirms the good suitability of the novel compounds for favorably modifying the properties of liquid-crystal mixtures, in this use example the melting point.

Use Example 2

The base mixture from Use Example 1 is treated with 10 mol % of the compound from Example 15; the melting point is lowered to 1° C., and the clearing point is raised to 86° C.

Use Example 3

A base mixture (TLC 1, Hoechst AG) having an X/$S_c$ transition at −35° C. and an N/I transition at 102° C. is treated with 10 mol % of the compound from Example 5; X/$S_c$ transition drops to −40° C., and the N/I transition rises to 106° C.

These two examples confirm the good suitability of the novel compounds for favorably modifying the properties of liquid-crystal mixtures, here the mesophase width.

We claim:

1. A trifluorophenylene compound of the formula (I)

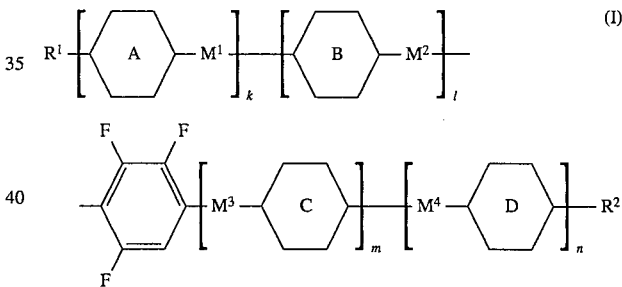

in which the symbols and indices have the following meanings:

R$^1$ and R$^2$ are, independently of one another, hydrogen, —F, —Cl or a straight-chain or branched alkyl radical having 1 to 20 carbon atoms (with or without asymmetrical carbon atoms), where one or more CH$_2$ groups may also be replaced by —O—, —CO—, —CH=CH—, —C≡C—, Δ or —Si(CH$_3$)$_2$—, with the proviso that oxygen atoms must not be bonded directly to one another, and/or where one or more H atoms of the alkyl radical may be substituted by —F; or are one of the radicals listed below:

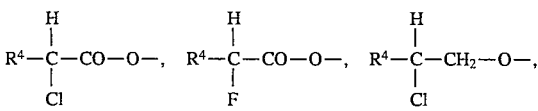

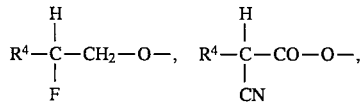

-continued

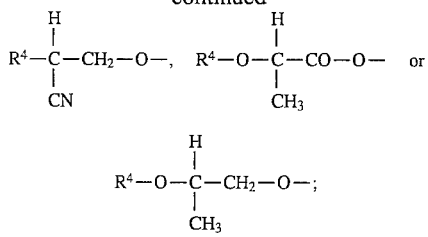

R$^4$ is hydrogen or a straight-chain or branched alkyl radical having 1–16 carbon atoms (with or without asymmetrical carbon atoms), where one CH$_2$ group may also be replaced by —O—;

M$^1$, M$^2$, M$^3$ and M$^4$ are identical or different and are
—CO—O—,
—O—CO—,
—OCCH$_2$CH$_2$—,

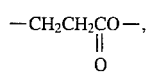

—(CH$_2$)$_4$—, —O(CH$_2$)$_3$—,
—(CH$_2$)—O—, —CH$_2$—O—, —O—CH$_2$—,
—C≡C—,
or a single bond;

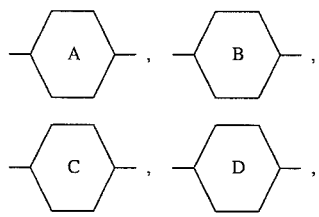

are identical or different and are 1,4-phenylene, in which one, two, three or four H atoms may be replaced by F, pyridine-2,5-diyl, in which one H atom may also be replaced by F, pyrimidine-2,5-diyl, in which one H atom may also be replaced by F, trans-1,4-cyclohexylene, in which one H atom may be replaced by CN or CH$_3$, 1,3,4-thiadiazole-2,5-diyl;

k, l, m and n are zero or one, with the proviso that the sum k+l+m+n is 1, 2 or 3;

with the proviso that if k and l are both zero R$^1$ must not be F, Cl, OCHF$_2$, or CF$_3$.

2. A compound as claimed in claim 1, wherein the symbols and indices have the following meanings:

R$^1$ and R$^2$, independently of one another, are H or alkyl having 1 to 20 carbon atoms, where one or more CH$_2$ groups may also be replaced by —O—, —CH=CH—, —CO—, —C≡C— or Si(CH$_3$)$_2$—, and one or more H atoms may be replaced by F; or are

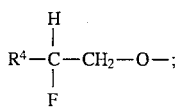

M$^1$, M$^2$, M$^3$ and M$^4$ are —CO—O—, —O—CO—, —CH$_2$—O—, —OCH$_2$—, —C≡C— or a single bond,

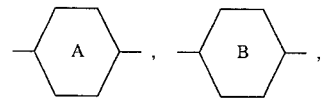

are 1,4-phenylene, where one, two or three H atoms may be replaced by F, pyrimidine-2,5-diyl, pyridine-2,5-diyl, 1,4-cyclohexylene or naphthalene-2,6-diyl; and k+l+m+n is 1 or 2;

with the proviso that if k and l are both zero R$^1$ must not be F, Cl, OCHF$_2$, or CF$_3$.

3. A compound as claimed in claim 1, wherein the symbols and indices have the following meanings:

R$^1$ and R$^2$ are alkyl having 1 to 16 carbon atoms, where one or more —CH$_2$— groups may also be replaced by —O—, —CH=CH— or —Si(CH$_3$)$_2$—, and one or more H atoms may be replaced by F;

M$^1$, M$^2$, M$^3$ and M$^4$ are —CO—O—, —O—CO— or a single bond,

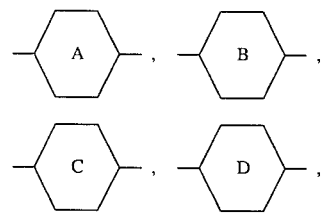

are 1,4-phenylene, where one, two or three H atoms may be replaced by F, pyrimidine-2,5-diyl, pyridine-2,5-diyl, 1,4-cyclohexylene or naphthalene-2,6-diyl; and k+l+m+n is 1 or 2;

with the proviso that if k and l are both zero R$^1$ must not be F, Cl, OCHF$_2$, or CF$_3$.

4. A ferroelectric liquid-crystalline mixture comprising from 2 to 35 components, of which at least one is a trifluorophenylene derivative as claimed in claim 1.

5. A ferroelectric liquid-crystalline mixture as claimed in claim 4, comprising from 0.01 to 80% by weight of one or more compounds as claimed in claim 1.

6. An electro-optical switching and/or display element, comprising two electrodes, two outer plates, at least one alignment layer and a compound as claimed in claim 1.

7. A process for preparing an electro-optical switching and/or display element which comprises filling a liquid-crystalline mixture as claimed in claim 4 with spacers between two glass substrates being provided with electrodes and one or two orientation layers.

8. An electro-optical switching and/or display element, comprising two electrodes, two outer plates, at least one alignment layer and a liquid-crystalline mixture as claimed in claim 4.

* * * * *